(12) United States Patent
Collen et al.

(10) Patent No.: US 7,445,775 B2
(45) Date of Patent: Nov. 4, 2008

(54) YEAST EXPRESSION VECTOR AND A METHOD OF MAKING A RECOMBINANT PROTEIN BY EXPRESSION IN A YEAST CELL

(75) Inventors: Désiré José Collen, London (GB); Nubuo Nagai, Leuven (BE); Yves Laroche, Brussel (BE)

(73) Assignee: Thromb-X nv, Leuven (BE)

( * ) Notice: Subject to any disclaimer, the term of this patent is extended or adjusted under 35 U.S.C. 154(b) by 386 days.

(21) Appl. No.: 10/450,976

(22) PCT Filed: Dec. 20, 2001

(86) PCT No.: PCT/BE01/00217

§ 371 (c)(1),
(2), (4) Date: Dec. 8, 2003

(87) PCT Pub. No.: WO02/50290

PCT Pub. Date: Jun. 27, 2002

(65) Prior Publication Data

US 2004/0071676 A1    Apr. 15, 2004

(30) Foreign Application Priority Data

| Dec. 21, 2000 | (GB) | .................. | 0031196.9 |
| Jul. 9, 2001 | (GB) | .................. | 0116690.9 |
| Jul. 9, 2001 | (GB) | .................. | 0116702.2 |

(51) Int. Cl.
*C12N 1/18* (2006.01)
*C12N 15/74* (2006.01)
*C07H 21/04* (2006.01)
*C07K 14/00* (2006.01)

(52) U.S. Cl. ................. 424/93.21; 435/254.2; 435/483; 435/320.1; 536/23.1; 530/350

(58) Field of Classification Search .............. 424/93.21; 435/254.2, 483, 320.1; 536/23.1; 530/350
See application file for complete search history.

(56) References Cited

U.S. PATENT DOCUMENTS

| 4,774,087 A | 9/1988 | Wu et al. |
| 5,288,489 A | 2/1994 | Reich et al. |
| 5,407,673 A | 4/1995 | Reich et al. |

FOREIGN PATENT DOCUMENTS

| WO | WO 90/13640 | 11/1990 |
| WO | WO 93/07893 | 4/1993 |
| WO | WO 94/10318 | 5/1994 |
| WO | WO 00/18436 | 4/2000 |

OTHER PUBLICATIONS

Song et al., Shengwu Gongcheng Xuebao (1999), 15(2) 211-214. abstract.*
Cregg et al., "Recombinant Protein Expression in *Pichia pastoris*," *Molecular Biology* 16:23-52 (2000).
Dunman et al. "O-Mannosylation of *Pichia pastoris* cellular and recombinant proteins," *Biotechnol. Appl. Biochem.* 28:39-45 (1998).
Wang et al., "Structure and function of microplasminogen: I. Methionine shuffling, chemical proteolysis, and proenzyme activation," *Protein Science* 4:1758-1767 (1995).
Cregg et al., "Recombinant protein expression in *Pichia pastoris*," Molecular Biotechnology 16 (1), 23-52 (2000).
Forsgren et al., "Molecular cloning and characterization of a full-length cDNA clone for human plasminogen," FEBS Lett. Mar. 23, 1987;213(2):254-60.
Lasters et al., "Enzymatic properties of phage-displayed fragments of human plasminogen," Eur. J. Biochem., 244, 946-952 (1997).
Thorsen et al., "Adsorption to fibrin of native fragments of known primary structure from human plasminogen," Biochimica et Biophsica Acta, 668 (1981) 377-387.
Wang et al., "Structure and function of microplasminogen: I. Methionine shuffling, chemical proteolysis, and proenzyme activation," Protein Sci. 1995 4: 1758-1767.
Shepard et al. "Large-Scale Purification of Recombinant Human Angiostatin." *Protein Expression and Purification* 20, 216-227 (2000).
European Patent Office Communication dated Jul. 19, 2006.
International Preliminary Examination Report dated Mar. 25, 2003.
International Search Report dated May 31, 2002.
English translation of Office Action as issued by Japan Patent Office dated Oct. 17, 2007 in Patent Application No. 067213/2007.

* cited by examiner

*Primary Examiner*—Chih-Min Kam
(74) *Attorney, Agent, or Firm*—Clark & Elbing LLP

(57) ABSTRACT

Vectors for the expression in yeast of mammalian plasminogen derivatives such as microplasminogen and miniplasminogen are presented. Methods for expression of these proteins in a methylotrophic yeast expression system are disclosed as well as the activation and stabilisation of the recombinant proteins. The proteins of this invention are used In the treatment of focal cerebral ischemic infarction and other thrombotic diseases.

32 Claims, 5 Drawing Sheets

FIGURE 3

```
              10              20              30              40
GCC CCT TCA TTT GAT TGT GGG AAG CCT CAA GTG GAG CCG AAG AAA TGT
 A   P   S   F   D   C   G   K   P   Q   V   E   P   K   K   C>

50              60              70              80              90
CCT GGA AGG GTT GTA GGG GGT TGT GTG GCC CAC CCA CAT TCC TGG CCC
 P   G   R   V   V   G   G   C   V   A   H   P   H   S   W   P>

100             110             120             130             140
TGG CAA GTC AGT CTT AGA ACA AGG TTT GGA ATG CAC TTC TGT GGA GGC
 W   Q   V   S   L   R   T   R   F   G   M   H   F   C   G   G>

150             160             170             180             190
ACC TTG ATA TCC CCA GAG TGG GTG TTG ACT GCA GCC CAC TGC TTG GAG
 T   L   I   S   P   E   W   V   L   T   A   A   H   C   L   E>

200             210             220             230             240
AAG TCC CCA AGG CCT TCA TCC TAC AAG GTC ATC CTA GGT GCA CAC CAA
 K   S   P   R   P   S   S   Y   K   V   I   L   G   A   H   Q>

250             260             270             280
GAA GTG AAT CTC GAA CCG CAT GTT CAG GAA ATA GAA GTG TCT AGG CTG
 E   V   N   L   E   P   H   V   Q   E   I   E   V   S   R   L>

290             300             310             320             330
TTC TTG GAG CCC ACA CGA AAA GAT ATT GCC TTG CTA AAG CTA AGC AGT
 F   L   E   P   T   R   K   D   I   A   L   L   K   L   S   S>

340             350             360             370             380
CCT GCC GTC ATC ACT GAC AAA GTA ATC CCA GCT TGT CTG CCA TCC CCA
 P   A   V   I   T   D   K   V   I   P   A   C   L   P   S   P>

390             400             410             420             430
AAT TAT GTG GTC GCC GAC CGG ACC GAA TGT TTC ATC ACT GGC TGG GGA
 N   Y   V   V   A   D   R   T   E   C   F   I   T   G   W   G>

440             450             460             470             480
GAA ACC CAA GGT ACT TTT GGA GCT GGC CTT CTC AAG GAA GCC CAG CTC
 E   T   Q   G   T   F   G   A   G   L   L   K   E   A   Q   L>

490             500             510             520
CCT GTG ATT GAG AAT AAA GTG TGC AAT CGC TAT GAG TTT CTG AAT GGA
 P   V   I   E   N   K   V   C   N   R   Y   E   F   L   N   G>

530             540             550             560             570
AGA GTC CAA TCC ACC GAG CTC TGT GCT GGG CAT TTG GCC GGA GGC ACT
 R   V   Q   S   T   E   L   C   A   G   H   L   A   G   G   T>

580             590             600             610             620
GAC AGT TGC CAG GGT GAC AGT GGA GGG CCT CTG GTT TGC TTC GAG AAG
 D   S   C   Q   G   D   S   G   G   P   L   V   C   F   E   K>

630             640             650             660             670
GAC AAA TAC ATT TTA CAA GGA GTC ACT AGT TGG GGT CTT GGC TGT GCA
 D   K   Y   I   L   Q   G   V   T   S   W   G   L   G   C   A>

680             690             700             710             720
CGC CCC AAT AAG CCT GGT GTC TAT GTT CGT GTC TCC AGG TTT GTT ACT
 R   P   N   K   P   G   V   Y   V   R   V   S   R   F   V   T>

730             740             750
TGG ATT GAG GGA GTG ATG AGA AAT AAT TAA
 W   I   E   G   V   M   R   N   N>
```

```
              10              20              30              40              50              60
GCA CCT CCG CCT GTT GTC CTG CTT CCA GAT GTA GAG ACT CCT TCC GAA GAA GAC TGT ATG
 A   P   P   P   V   V   L   L   P   D   V   E   T   P   S   E   E   D   C   M 70              80              90             100             110             120
TTT GGG AAT GGG AAA GGA TAC CGA GGC AAG AGG GCG ACC ACT GTT ACT GGG ACG CCA TGC
 F   G   N   G   K   G   Y   R   G   K   R   A   T   T   V   T   G   T   P   C 130             140             150             160             170             180
CAG GAC TGG GCT GCC CAG GAG CCC CAT AGA CAC AGC ATT TTC ACT CCA GAG ACA AAT CCA
 Q   D   W   A   A   Q   E   P   H   R   H   S   I   F   T   P   E   T   N   P 190             200             210             220             230             240
CGG GCG GGT CTG GAA AAA AAT TAC TGC CGT AAC CCT GAT GGT GAT GTA GGT GGT CCC TGG
 R   A   G   L   E   K   N   Y   C   R   N   P   D   G   D   V   G   G   P   W 250             260             270             280             290             300
TGC TAC ACG ACA AAT CCA AGA AAA CTT TAC GAC TAC TGT GAT GTC CCT CAG TGT GCG GCC
 C   Y   T   T   N   P   R   K   L   Y   D   Y   C   D   V   P   Q   C   A   A 310             320             330             340             350             360
CCT TCA TTT GAT TGT GGG AAG CCT CAA GTG GAG CCG AAG AAA TGT CCT GGA AGG GTT GTA
 P   S   F   D   C   G   K   P   Q   V   E   P   K   K   C   P   G   R   V   V 370             380             390             400             410             420
GGG GGG TGT GTG GCC CAC CCA CAT TCC TGG CCC TGG CAA GTC AGT CTT AGA ACA AGG TTT
 G   G   C   V   A   H   P   H   S   W   P   W   Q   V   S   L   R   T   R   F 430             440             450             460             470             480
GGA ATG CAC TTC TGT GGA GGC ACC TTG ATA TCC CCA GAG TGG GTG TTG ACT GCA GCC CAC
 G   M   H   F   C   G   G   T   L   I   S   P   E   W   V   L   T   A   A   H 490             500             510             520             530             540
TGC TTG GAG AAG TCC CCA AGG CCT TCA TCC TAC AAG GTC ATC CTA GGT GCA CAC CAA GAA
 C   L   E   K   S   P   R   P   S   S   Y   K   V   I   L   G   A   H   Q   E 550             560             570             580             590             600
GTG AAT CTC GAA CCG CAT GTT CAG GAA ATA GAA GTG TCT AGG CTG TTC TTG GAG CCC ACA
 V   N   L   E   P   H   V   Q   E   I   E   V   S   R   L   F   L   E   P   T 610             620             630             640             650             660
CGA AAA GAT ATT GCC TTG CTA AAG CTA AGC AGT CCT GCC GTC ATC ACT GAC AAA GTA ATC
 R   K   D   I   A   L   L   K   L   S   S   P   A   V   I   T   D   K   V   I
```

Figure 4A

```
              670         680         690         700         710         720
CCA GCT TGT CTG CCA TCC CCA AAT TAT GTG GTC GCC GAC CGG ACC GAA TGT TTC ATC ACT
 P   A   C   L   P   S   P   N   Y   V   V   A   D   R   T   E   C   F   I   T 730         740         750         760         770         780
GGC TGG GGA GAA ACC CAA GGT ACT TTT GGA GCT GGC CTT CTC AAG GAA GCC CAG CTC CCT
 G   W   G   E   T   Q   G   T   F   G   A   G   L   L   K   E   A   Q   L   P 790         800         810         820         830         840
GTG ATT GAG AAT AAA GTG TGC AAT CGC TAT GAG TTT CTG AAT GGA AGA GTC CAA TCC ACC
 V   I   E   N   K   V   C   N   R   Y   E   F   L   N   G   R   V   Q   S   T 850         860         870         880         890         900
GAG CTC TGT GCT GGG CAT TTG GCC GGA GGC ACT GAC AGT TGC CAG GGT GAC AGT GGA GGG
 E   L   C   A   G   H   L   A   G   G   T   D   S   C   Q   G   D   S   G   G 910         920         930         940         950         960
CCT CTG GTT TGC TTC GAG AAG GAC AAA TAC ATT TTA CAA GGA GTC ACT AGT TGG GGT CTT
 P   L   V   C   F   E   K   D   K   Y   I   L   Q   G   V   T   S   W   G   L 970         980         990        1000        1010        1020
GGC TGT GCA CGC CCC AAT AAG CCT GGT GTC TAT GTT CGT GTC TCC AGG TTT GTT ACT TGG
 G   C   A   R   P   N   K   P   G   V   Y   V   R   V   S   R   F   V   T   W 1030        1040
ATT GAG GGA GTG ATG AGA AAT AAT TAA
 I   E   G   V   M   R   N   N   >
```

Figure 4B

YEAST EXPRESSION VECTOR AND A METHOD OF MAKING A RECOMBINANT PROTEIN BY EXPRESSION IN A YEAST CELL

CROSS REFERENCE TO RELATED APPLICATIONS

This application is the U.S. National Stage of International Application No. PCT/BE01/00217, filed Dec. 20, 2001, which was published in English under PCT Article 21(2), and which claims the benefit of British Patent Application Nos. 0031196, 0116690, 0116702, filed Dec. 21, 2000, Jul. 9, 2001, and Jul. 9, 2001, respectively.

This invention relates to the treatment and prevention of thrombotic disorders. More specifically, the present invention relates to the high yield production, via recombinant DNA technology, of derivatives of mammalian plasminogen, their purification and stabilization, and to the use of the corresponding activated and stabilized plasmin derivatives for the treatment of focal cerebral ischemic infarction (ischemic stroke) or arterial thrombotic diseases such as peripheral arterial occlusive disease or acute myocardial infarction.

BACKGROUND OF THE INVENTION

Mammalian blood contains an enzymatic system, called the fibrinolytic or plasminogen system, which plays a role in various biological phenomena such as reproduction, embryogenesis, cell invasion, angiogenesis and brain function. In addition, this system participates in thrombosis, atherosclerosis, neoplasia, metastasis and chronic inflammatory disorders. The fibrinolytic system contains plasminogen, which by the action of plasminogen activators is converted to the active enzyme plasmin, which in turn digests fibrin to soluble degradation products. Two physiological plasminogen activators, respectively called tissue-type (t-PA) and urokinase-type (u-PA), have been identified. Inhibition of the fibrinolytic system may occur either at the level of plasminogen activators, by means of specific plasminogen activator inhibitors (PAI), or at the level of plasmin, mainly by means of $\alpha_2$-antiplasmin.

A number of substances are involved in clot formation and lysis. Plasminogen and plasmin are two of the primary substances involved in lysis. Plasminogen, a protein composed of 791 amino-acids that circulates in plasma at a concentration of about 200 μg/ml, is the zymogen form of a fibrinolytic enzyme, plasmin, which has broad substrate specificity and is ultimately responsible for degrading blood clots. For the most part, fibrin proteolysis is mediated by the generation of plasmin within a fibrin clot from the plasminogen trapped within the clot. Plasminogen-plasmin conversion, both within a clot and at its surface, is facilitated by the affinity of t-PA for fibrin, which results in a fibrin-dependent t-PA-induced plasminogen activation.

Plasminogen is a single-chain glycoprotein with a molecular weight of 92,000 which is synthesized by the liver and cleared from the circulation (via the liver) with a half-life of about 2.2 days. Human plasminogen comprises (i) a pre-activation peptide of about 67 to 76 amino-acids, (ii) five triple-loop disulfide bonded structures (named "kringles") of about 80 amino-acids, (iii) a catalytic serine proteinase unit of about 230 amino-acids, and (iv) some inter-domain connecting sequences. Native plasminogen with $NH_2$-terminal glutamic acid (commonly named "Glu-plasminogen") is easily converted by limited digestion by plasmin of the $Arg^{68}$-$Met^{69}$, $Lys^{77}$-$Lys^{78}$, or $Lys^{78}$-$Val^{79}$ peptide bonds to modified forms commonly designated "Lys-plasminogen". Plasminogen is converted to plasmin by cleavage of the $Arg^{561}$-$Val^{562}$ peptide bond. The plasmin molecule is a two-chain trypsin-like serine proteinase with an active site composed of $His^{603}$, $Asp^{646}$, and $Ser^{741}$. The kringles of plasminogen contain lysine binding sites that interact specifically with amino-acids such as lysine, 6-aminohexanoic acid and tranexamic acid. The lysine binding sites located in the kringle 1-3 region mediate the specific binding of plasminogen to fibrin and the kinetics of the interaction of plasmin with $\alpha_2$-antiplasmin, and therefore play a crucial role in the regulation of physiological fibrinolysis.

Miniplasminogen is a derivative of plasminogen lacking the first four kringles which may be prepared by digestion of plasminogen with elastase and which is fully activatable to plasmin. It has a molecular weight of 38,000 and contains over 100 amino-acids of the A chain including the fifth kringle structure.

Elevated pH conditions result in cleaving the $Arg^{530}$-$Lys^{531}$ or $Lys^{531}$-$Leu^{532}$ bond of plasminogen and promoting disulfide bond rearrangement, thus producing microplasminogen, a derivative consisting of a 30 or 31 residue COOH-terminal peptide derived from the A chain bound through new disulfide bonds to the intact B-chain of plasmin, as disclosed in U.S. Pat. No. 4,774,087.

$\alpha_2$-antiplasmin is the main physiological plasmin inhibitor in human plasma which very rapidly inhibits plasmin, whereas plasmin formed in excess of $\alpha_2$-antiplasmin may be neutralized more slowly by macroglobulin and other serine proteinase inhibitors. $\alpha_2$-antiplasmin is a single-chain glycoprotein containing 464 amino acids which is present in plasma at a concentration of about 70 mg/l. During purification it is usually converted into a 452 amino-acid derivative by removal of 12 amino terminal amino-acids. $\alpha_2$-antiplasmin is synthesized by the liver and cleared from the circulation (via the liver) with a half-life of 2.6 days. Its reactive site is the $Arg^{376}$-$Met^{377}$ peptide bond. $\alpha_2$-antiplasmin is unique among serine proteinase inhibitors by having a COOH-terminal extension of 51 amino-acid residues which contains a secondary binding site that reacts with the lysine binding sites of plasminogen and plasmin. The native plasminogen-binding form of $\alpha_2$-antiplasmin becomes partly converted in the circulating blood to a non-plasminogen-binding, less reactive form, which lacks the 26 COOH-terminal residues. The $Gln^{14}$-residue of $\alpha_2$-antiplasmin can crosslink to $\alpha$-chains of fibrin by a process which requires $Ca^{2+}$ and is catalyzed by activated coagulation factor XII. $\alpha_2$-antiplasmin forms an inactive 1:1 stoichiometric complex with plasmin.

Plasmin or derivatives thereof (including mini- and microplasminogen), when infused in the vicinity of a clot in a dose sufficiently high to deplete $\alpha_2$-antiplasmin locally in an occluded blood vessel with stagnant flow, may have a sufficiently long half-life to be able to exert a local therapeutic effect. The administration of large amounts of plasmin is well tolerated, unlike the use of certain other proteolytic enzymes.

Thromboembolic disease, i.e. blockage of a blood vessel by a blood clot, affects many adults and can be a cause of death. Most spontaneously developing vascular obstructions are due to the formation of intravascular blood clots, known as thrombi. Small fragments of a clot (emboli) may detach from the body of the clot and travel through the circulatory system to lodge in distant organs and initiate further clot formation. Heart attack, stroke, renal and pulmonary infarcts are well known consequences of thromboembolic phenomena. A blood clot is a gelled network of protein molecules within which are trapped circulating blood cells, platelets and plasma proteins. Fibrin is a major protein component of a clot which forms a relatively Insoluble network. Proteolytic, particularly fibrinolytic enzymes, have been used to dissolve vascular obstructions, since disruption of the fibrin matrix results in dissolution of the clot. Clots are formed when soluble fibrinogen, which is present in high concentrations in blood, is converted to insoluble fibrin by the action of thrombin. The probability of clot formation can be reduced by lowering the concentration of circulating fibrinogen, using fibrinogenolytic enzymes. Thromboembolytic therapies have involved the administration of a plasminogen activator, e.g. either by direct intravenous injection, or by reinjection of a patient's plasma to which a plasminogen activator has been added ex vivo, or injection of plasma protein fractions previously mixed with streptokinase, or injection of porcine plasmin stabilized with added lysine in conjunction with streptokinase.

Stroke is defined as a rapidly developing clinical sign of focal or global disturbance of cerebral function with symptoms lasting at least 24 hours. Stroke is typically caused by blockage or occlusion of blood vessels to the brain or within the brain. With complete occlusion, arrest of cerebral circulation causes cessation of neuronal electrical activity within seconds. Within a few minutes after deterioration, depletion of high energy phosphates, membrane ion pump failure, efflux of cellular potassium, influx of sodium chloride and water, and membrane depolarization occur. If the occlusion persists for more than five to ten minutes, irreversible damage results. With incomplete ischemia, however, the outcome is difficult to evaluate and depends largely on residual perfusion and the availability of oxygen. After a thrombotic occlusion of a cerebral vessel, ischemia is rarely total. Some residual perfusion usually persists in the ischemic area, depending on collateral blood flow and local perfusion pressure.

Cerebral blood flow can compensate for drops in mean arterial blood pressure from 90 to 60 mm Hg by auto-regulation. This phenomenon involves dilatation of downstream resistant vessels. Below 60 mm Hg, vasodilatation is inadequate and the cerebral blood flow falls. The brain however has perfusion reserves that can compensate for the fall in cerebral blood fall. When distal blood pressure falls below about 30 mm Hg, both compensatory mechanisms (auto-regulation and perfusion reserve) are inadequate to prevent failure of oxygen delivery. As flow drops below the ischemic threshold, symptoms of tissue hypoxia develop. Severe ischemia may be lethal. Moderate ischemia results in a tissue area that can be saved called penumbra. In the neurological context, penumbra refers to a zone of brain tissue with moderate ischemia and paralyzed neuronal function, which is reversible with restoration of adequate perfusion. The penumbra forms a zone of collaterally perfused tissue surrounding a core of severe ischemia in which an infarct has developed. When a clot is degraded and the blood flow to the penumbra is restored, the phenomenon of reperfusion injury can occur.

Although an ischemic event can occur anywhere in the vascular system, the carotid artery bifurcation and the origin of the internal carotid artery are the most frequent sites for thrombotic occlusions of cerebral blood vessels, which result in cerebral ischemia. The symptoms of reduced blood flow due to stenosis or thrombosis are similar to those caused by middle cerebral artery disease. Flow through the ophthalmic artery is often affected sufficiently to produce transient monocular blindness. Severe bilateral internal carotid artery stenosis may result in cerebral hemispheric hypoperfusion. This manifests with acute headache ipsilateral to the acutely ischemic hemisphere. Occlusions or decrease of the blood flow with resulting ischemia of one anterior cerebral artery distal to the anterior communicating artery produces motor and cortical sensory symptoms in the contralateral leg and, less often, proximal arm. Other manifestations of occlusions or underperfusion of the anterior cerebral artery include urinary incontinence due to damage to the parasagittal frontal lobe. Language disturbances manifested by decreased spontaneous speech may accompany generalized depression of psychomotor activity.

Most ischemic strokes involve portions or all of the territory of the middle cerebral artery, with emboli from the heart or extracranial carotid arteries accounting for most cases. Emboli may occlude the main stem of the middle cerebral artery, but more frequently produce distal occlusion of either the superior or the inferior branch. Occlusions of the superior branch cause weakness and sensory loss that are greatest in the face and arm. Occlusions of the posterior cerebral artery distal to its penetrating branches cause complete contra-lateral loss of vision. Difficulty in reading (dyslexia) and performing calculations (dyscalculia) may follow ischemia of the dominant posterior cerebral artery. Proximal occlusion of the posterior cerebral artery causes ischemia of the branches penetrating to calamic and limbic structures, resulting in disturbances that may chronically change to intractable pain of the defective site (thalamic pain).

A significant event in cerebral ischemia is known as the transient ischemic attack ("TIA"), defined as a neurologic deficit with a duration of less than 24 hours. TIA is an important sign of an ischemic development that may lead to cerebral infarction. Its etiology involves hemodynamic events and thromboembolic mechanisms. Because TIA often resolves within one hour, a longer deficit is often classified as presumptive stroke and is, accordingly, associated with permanent brain injury. Therefore, computed tomographic brain scans are used to search for cerebral infarction in areas affected by TIA lasting longer than two hours. Thus, the relevant clinical distinction between TIA and stroke is whether ischemia has caused brain damage, which is typically classified as infarction or ischemic necrosis. Subjects with deteriorating clinical signs might have stroke in evolution (progressive stroke).

Many other diseases are caused by or associated with ischemia. For instance, vertebrobasilar ischemia results from occlusion of the vertebral artery which causes lateral medullary syndrome with symptoms including vertigo, nausea, ipsilateral ataxia and Herner's syndrome. Vertebrobasilar ischemia often produces multifocal lesions scattered on both sides of the brain stem along a considerable length. A basilar artery occlusion produces massive deficits, including paralysis of the limbs and of most bulbar muscles, leaving the subject only able to communicate by moving the eyes or eyelids and producing an initial reduction in arousal followed by blindness and amnesia.

Venous occlusion can cause massive damage and death. The primary mechanism of brain damage is then a reduction in capillary blood flow because of increased outflow resistance from the blocked veins. Back transmission of high pressure into the capillary bed usually results in early brain swelling from oedema and hemorrhagic infarction in subcortical white matter. The most dangerous form of venous disease arises when the superior sagittal sinus is occluded. Venous occlusion occurs in association with coagulation disorders, often in the purpural period or in subjects with disseminated cancers.

Brief diffuse cerebral ischemia can cause syncope without any permanent sequel. Prolonged diffuse ischemia in other organs has devastating consequences. Common causes are cardiopulmonary failure, including infarction, aortic dissection and global hypoxia or carbon monoxide poisoning. Clinically, a diffuse hypoxia/ischemia results in unconsciousness and coma, often followed by a chronic vegetative state. If the subject does not regain consciousness within a few days, chances for the return of independent brain functions becomes very poor.

Hyperviscosity syndrome is another disease related to blood flow and ischemia. Subjects with hyperviscosity syndrome can present either with focal neurologic dysfunction or with diffuse or multifocus signs or symptoms including headache, visual disturbances, cognitive impairments or seizures.

Ischemic stroke due to thrombotic closure of a cerebral artery is amenable to therapy with antithrombotic and thrombolytic agents. The use of t-PA within three hours of symptom onset is associated with a better neurologic outcome, but a significant percentage of treated patients experience acute hemorrhage in the brain. Thus, the development of safer and more effective treatments is needed.

U.S. Pat. No. 5,288,489 discloses a method of dissolving an intravascular thrombus in a human patient, or reducing the risk of thrombus formation in a patient (such as diabetics and pregnant women), comprising administering parenterally to the patient a therapeutically effective amount of human or mammalian plasmin or mini-plasmin or micro-plasmin in a fibrinolytic or fibrinogenolytic active form, the said active form being obtained either by exposure to an insolubilized, entrapped, encapsulated or immobilized plasminogen activator or by inhibiting the autolytic activity by means of certain hydrophobic ions. This method is disclosed in the context of heart attack, stroke, renal and pulmonary infarctions, thrombophlebitis, and so on. EP-A-631,786 discloses administration to a subject of a protein having the effect of lys-plasminogen for the treatment of ischemia, infarction, brain edema and reperfusion injury that follows ischemic events. WO 00/18436 discloses the use of plasmin, mini-plasmin or micro-plasmin in a therapeutic composition for the treatment of focal cerebral ischemic infarction (ischemic stroke).

In the population over 60 years of age, the prevalence of intermittent claudication or chronic peripheral arterial occlusive disease (PAOD) being the result of atherosclerotic and thrombotic processes, is between 1 and 8%. Over the course of their disease, about 20% of the patients with intermittent claudication will progress to critical leg ischemia (acute PAOD) endangering the viability of the lower extremity, 10% will undergo invasive/surgical procedures for progressive symptoms, and 5% require amputation of the limb. Blood flow can be restored through operative bypass surgery, vascular repair surgery or pharmacological dissolution of the blood clot. Intra-arterial thrombolysis is expected to provide a significant reduction in surgical procedures, without increased risk of amputation or death. Urokinase is currently the most widely used agent for intra-arterial thrombolysis.)

Plasminogen can be obtained from human plasma fractions by affinity chromatography on lysine-Sepharose, however with yields of no more than 0.25 g/l. With the general reluctance to use plasma fractionation derivatives, alternative approaches such as production via recombinant DNA technology are preferred. For the production of a large and complex molecule such as plasminogen or plasmin, however, an effective expression system is required. Indeed recombinant Intact plasminogen cannot readily be expressed in activatable form in common eukaryotic expression systems, due to the nearly ubiquitous presence of intracellular plasminogen activators within such cell types, resulting in degradation of human plasminogen in the conditioned cell culture media. According to J. Wang et al. in Protein Science (1995) 4:1758-1767, a baculovirus/insect cell expression system has enabled expression of microplasminogen at low levels of 3 to 12 mg/l. Such a yield is obviously too low for the production of large quantities of the purified active substance. We are not aware of any data relating to the expression of miniplasminogen. Therefore, there is a need in the art for an expression system making it possible to produce large amounts of plasminogen and derivatives thereof, including mini- and microplasminogen, which will be useful in the treatment of ischemic and thrombotic disorders and associated diseases such as listed hereinabove.

SUMMARY OF THE INVENTION

The present invention relates to the use of certain yeast, e.g. *Pichia pastoris*, for the high yield production of recombinant mammalian plasminogen and derivatives thereof (including, but not limited to, miniplasminogen and to microplasminogen) and to the production of recombinant mammalian plasmin and derivatives thereof in sufficient amounts, purity and stability to be clinically applicable for the treatment of mammal, specifically humans and horses. The therapeutic efficacy of the recombinant human microplasmin obtained according to this production method was illustrated in animal models of ischemic stroke, acute myocardial infarction and extracorporeal arteriovenous circulation thrombosis models.

BRIEF DESCRIPTION OF THE DRAWINGS

FIG. 3 shows the nucleotide sequence (SEQ. ID. No. 3) and amino-acid sequence (SEQ. ID. No. 4) of human microplasminogen.

FIG. 4 shows the nucleotide sequence (SEQ. ID. No. 5) and amino-acid sequence (SEQ. ID. No. 6) of human miniplasminogen.

Definitions

Figure 1:
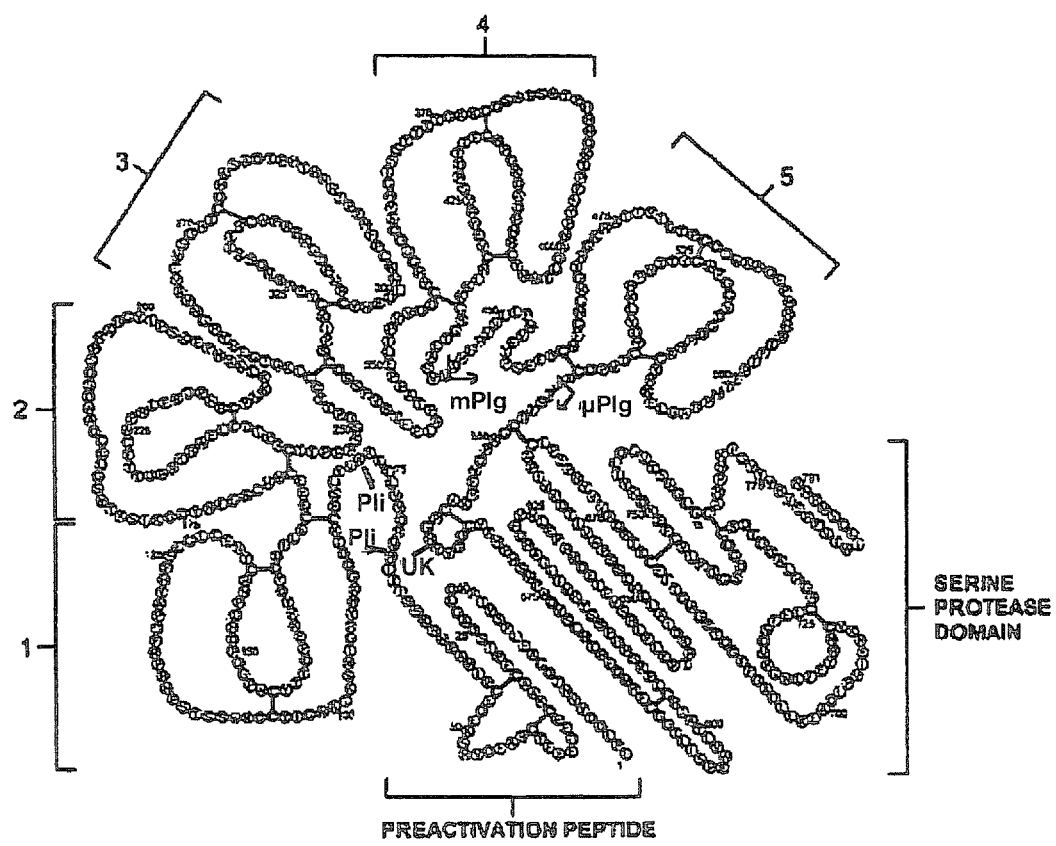
FIG. 1 is a schematic representation of the amino-acid structure of plasminogen, wherein black bars indicate disulphide bonds; Pli is a plasmic cleavage site for conversion of Glu-plasminogen to Lys-plasminogen; UK is the cleavage site for plasminogen activators, yielding plasmin; μPlg and mPlg respectively indicate the origin of microplasminogen and miniplasminogen used in this invention.

The term "catalytic domain of plasminogen", as used herein, refers to a serine protease unit of about 230 amino-acids that, after activation by a plasminogen activator, digest fibrin to soluble degradation products.

The term "mutants", as used herein, refers to a catalytically active protein sequence in which one or more amino-acids are substituted, deleted or mutated, and wherein the level of similarity with the wild-type protein is at least 80%, preferably at least 85% and more preferably at least 90%.

The term "hybrids", as used herein, refers to the protein of a mammal wherein at least one sequence of one or more amino-acids is replaced by a sequence, preferably the corresponding sequence, from the corresponding protein of another mammal. With respect to plasminogen, the sequence replacement may be either in the catalytic domain or in any of the five kringle domains.

DETAILED DESCRIPTION OF THE INVENTION

A first object of the invention is a yeast expression vector comprising a mammalian nucleotide sequence operably linked to a promoter, wherein the said mammalian nucleotide sequence codes for the catalytic domain of plasminogen and further optionally codes for one of more kringle domains of plasminogen, or mutants or hybrids thereof. In preferred embodiments of the said yeast expression vector, the mammalian nucleotide sequence codes for plasminogen, microplasminogen and miniplasminogen respectively. In a more specific embodiment, the nucleotide sequence, such as SEQ ID No. 1 (plasminogen), SEQ ID No. 3 (microplasminogen) or SEQ ID No. 5 (miniplasminogen). In a preferred embodiment, the promoter is an inducible promoter. In another preferred embodiment, the yeast expression vector is able to stable integrate in the yeast genome, e.g. by homologous recombination. In preferred embodiments, the nucleotide sequence is fused to a secretion signal, i.e. a peptide that targets protein to the cell membrane where the signal peptide is cleaved and the protein released in the medium, for example α-factor, PHO or AGA-2.

Insert the enclosed sequence listing at the end of the specification.

Preferably, the yeast expression vector of the invention is for expression in a yeast selected from the group consisting of methylotrophic yeasts represented by the genera *Hansenula, Pichia, Candida* and *Torulopsis*.

A second object of the invention is a yeast cell comprising a mammalian nucleotide sequence coding for the catalytic domain of plasminogen and further optionally coding for one or more kringle domains of plasminogen, or mutants or hybrids thereof. In preferred embodiments of the said yeast cell, the mammalian nucleotide sequence codes for plasminogen, microplasminogen and miniplasminogen respectively, i.e. the yeast cell comprises the nucleotide sequence SEQ.ID.No. 1 or the nucleotide sequence SEQ.ID.No. 3 or the nucleotide sequence SEQ.ID.No. 5.

The invention also relates to a yeast cell transfected with a vector such as disclosed hereinabove. Preferably, the said vector is integrated in th genome.

The yeast cell of the invention preferably belongs to the group of methylotrophic yeasts. More particularly, the said yeast may be selected from the genera consisting of, *Pichia, Hansenula, Candida*, and *Torulopsis*. In another embodiment, the yeast cell of the invention belongs to the *Pichia pastoris* species.

An exemplary yeast cell belongs to *Pichia Pastoris* the cell line X33(pPicZalpha-MPG1)#5 deposited on Dec. 5, 2001 with the Belgian Coordinated Collections of Micro-organisms [BCCM-MUCL, Place Croix du Sud 3, B-1348, Louvain La Neuve, Belgium] under accession number MUCL43676. A most significant advantage of the yeast cells of the invention is their ability to express human microplasminogen at a level of at least about 100 mg/litre, i.e. at a much higher level than was known in the art. Another advantage is their ability to express human miniplasminogen at a level of at least about 3 mg/litre.

Another object of the invention is a method of expressing a mammalian protein comprising the catalytic domain of plasminogen and further optionally comprising one or more kringle domains of plasminogen, or mutants or hybrids thereof, in a yeast cell such as defined hereinabove, using recombinant technology procedures well known in the art which are detailed in the appended examples. Specific embodiments of the said method relate to mammalian proteins having respectively the amino-acid sequence SEQ.ID. No. 2 (human plasminogen), the amino-acid sequence SEQ.ID. No. 4 (human micro-plasminogen) or the amino-acid sequence SEQ.ID. No. 6 (human mini-plasminogen). In a preferred embodiment, the method further comprises the step of activating the expressed mammalian protein by means of a plasminogen activator which may be staphylokinase or a variant thereof. In another preferred embodiment, the method further comprises the step of stabilizing the expressed and activated mammalian protein by means of a stabilizing agent. The said stabilizing agent may comprise either an amino-acid selected from the group consisting of lysine, 6-amino hexanoic acid and tranexamic acid or a stabilizing medium. The latter may suitably be an acid solution or an acid buffer such as a citrate buffer with a pH of about 3.1. Still preferred is a m thod further comprising the step of drying the expressed, activated and stabilized mammalian protein, e.g. by means of lyophilization.

The present invention also relates to a recombinant mammalian protein obtained by a method such as described hereinabove or expressed in a yeast cell such as defined hereinabove. This protein is obtainable in large amounts and in a high purity level, thus meeting the necessary requirements for being used as an active ingredient in pharmaceutical compositions for the treatment of the various ischemic diseases listed in the above section "background of the invention".

The present invention will be demonstrated in more detail in the following examples, which are however not intended to be limiting the scope of the invention, the latter being only defined by the appended claims.

EXAMPLE 1

Vector Construction for Expression of Human Microplasminogen and Human Miniplasminogen in *Pichia pastoris*

The pPICZαA secretion vector purchased from Invitrogen Corporation (Carlsbad, Calif.) was used to direct expression and secretion of recombinant human microplasminogen in *Pichia pastoris*. Relevant features of this vector are:

- a 942 bp fragment containing the alcohol oxidase 1 (AOX1) promoter that allows methanol-inducible, high level expression in Pichia and targeted plasmid integration to the AOX1 chromosomal locus,
- the native transcription termination and polyadenylation signal from the AOX1 gene;
- an expression cassette conferring zeocin resistance to *Escherichia coli* and *Pichia pastoris*;
- a ColE1 origin of replication for propagation and maintenance of the plasmid in *E. coli*, and
- unique restriction sites (Sacl, Pmel, BstXI) that permit linearization of the vector at the AOX1 locus for efficient integration into the *Pichia* genome.

In addition to the above features, this vector contains the secretion signal of the *Saccharomyces cerevisiae* α-factor prepropeptide, allowing expression of heterologous proteins as secreted proteins in the medium. The processing of the α factor mating signal sequence in pPICZα occurs in two steps:

1. the preliminary cleavage of the signal sequence by the KEX2 gene product, with the Kex2 cleavage occuring between arginine and glutamine in the sequence Glu-Lys-Arg * Glu-Ala-Glu-Ala [SEQ ID. NO: 11] wherein * is the site of cleavage.
2. the Glu-Ala repeats are further cleaved by the STE13 gene product.

However, the Glu-Ala repeats are not always necessary for cleavage by Kex2, depending on the amino acid following the Glu-Lys-Arg sequence. In some cases where Ste13 cleavage is not efficient, the Glu-Ala repeats are left on the $NH_2$-terminus of the expressed protein of interest.

A XhoI recognition sequence is present at the COOH-terminus of the α factor secretion signal, immediately upstream of the Lys-Arg Kex2 cleavage site. This XhoI restriction site may be used to clone the gene of interest flush with the Kex2 cleavage site by using a PCR cloning approach and an appropriate forward primer to rebuild the sequence from the XhoI site to the arginine codon. The recombinant protein of interest will then be expressed with a native $NH_2$-terminus. Engineered immediately downstream of the α factor signal sequence in the pPICZαA vector is a multi-cloning site with recognition sequences for the enzymes EcoRI, SfiI, KpnI, XhoI, SacII and XbaI to facilitate the cloning of foreign genes.

Expression Vector Construction for Microplasminogen

The vector Fmyc-μPli disclosed by Lasters et al. in *Eur. J. Biochem*. (1997) 244:946 was used to isolate, by amplification ("PCR-rescue") with the Advantage cDNA polymerase mix available from Clontech (Palo Alto, Calif.), the region encoding the human microplasminogen protein. After a DNA template denaturation step of 3 minutes at 94° C., 30 temperature cycles were performed (30 seconds at 94° C., 30 seconds at 50° C., 30 seconds at 72° C.), followed by a 2 minutes final elongation step at 72° C. The following oligonucleotide primers LY-MPG1 (sense) and LY-MPG2 (antisense) were used in this reaction:

```
LY-MPLG1: 5' GGGGTATCT CTC GAG AAA AGA GCC CCT TCA TTT GAT TG   (SEQ.ID. No.7)

LY-MPLG2: 5' GTTTTTGT TCT AGA TTA ATT ATT TCT CAT CAC TCC CTC   (SEQ.ID. No.8)
```

The LY-MPLG1 primer had an annealing region corresponding to residues 543-548 of plasminogen (Ala-Pro-Ser-Phe-Asp-Cys) [SEQ ID. NO: 12] preceded by a non-annealing extension which included the last four residues of the α factor mating signal (Leu-Glu-Lys Arg) [SEQ ID. NO: 13]. In this extension, the Leu-Glu codons determine the Xho I restriction site (underlined) allowing the cloning of the gene of interest flush with the Kex2 cleavage site. The LY-MPLG2 primer had an annealing region corresponding to the last seven residues of plasminogen, followed by a TAA stop-codon and a non-annealing region comprising a XbaI recognition sequence.

The amplified fragment having the expected size (~780 bp) was digested with XhoI and XbaI, and directionally cloned into the vector pPICZαA. The recipient vector-fragment was prepared by XhoI and XbaI restriction, and purified from agarose gel using the Qiaquick gel extraction kit (Qiagen GmbH, Germany). The *E. coli* strain TG1 (DSMZ collection #1208, Germany) was transformed with the ligation mixture, and zeocin resistant clones were selected. Based on restriction analysis, a plasmid clone containing an insert of the expected size was retained for further characterization. Sequence determination of the vector pPICZα-MPLG1 (clone #5) confirmed the precise insertion of the microplasminogen coding region fused to the a factor mating signal, as wel as the absence of unwanted mutations in the coding region. The primers 5'AOX and 3'AOX were provided in the EasySelect *Pichia* expression kit from Invitrogen, Carlsbad, Calif.

The determined nucleotide sequence and the deduced amino-acid sequence of human microplasminogen used are represented in SEQ.ID No. 3 and SEQ.ID No. 4, respectively. Compared to the sequence previously determined by Forsgren et al. in FEBS Lett. (1987) 213: 254, the nucleotide sequence differs in 10 positions. However, the amino acid sequence was identical.

Expression Vector Construction for Miniplasminogen

A pPICZα-derived secretion vector was constructed as follows for miniplasminogen expression, making use of the hereinabove described pPICZα-MPLGI vector.

The vector FdTet-SN-miniPIg disclosed by Lasters et al. (cited supra) was used to isolate by amplification ("PCR-rescue") a 500 bp DNA fragment encoding kringle five and part of the catalytic domain of the miniplasminogen protein. After a DNA template denaturation step of 3 minutes at 94° C., 30 temperature cycles were performed (10 seconds at 94° C., 10 seconds at 50° C., 15 seconds at 72° C.), followed by a 2 minutes final elongation step at 72° C. The following oligonucleotide primers LY-MINPLG1 (sense) and LY-MINPLG2 (antisense) were used in this reaction:

non-annealing extension which included the last four residues of the factor mating signal (Leu-Glu-Lys-Arg) [SEQ ID. NO: 13]. In this extension, the Leu-Glu codons determine the Xho I restriction site allowing the cloning of the gene of interest flush with the Kex2 cleavage site.

The LY-MINPLG2 primer has an annealing region corresponding to the residues 596-604 of plasminogen (Glu-Trp-Val-Leu-Thr-Ala-Ala-His-Cys) [SEQ ID. NO: 15]. This annealing region of the catalytic domain, also present in the microplasminogen expression vector, comprises a unique Pst I recognition sequence (underlined).

The amplified fragment having the expected size was digested with XhoI and PstI, and directionally cloned into the vector pPICZα-MPLG1 described above (microplasmin expression vector). The recipient vector-fragment was prepared by XhoI and PstI restriction, and purified from agarose gel using the Qiaquick gel extraction kit (Qiagen GmbH, Germany). The *E. coli* strain TGI (DSMZ collection #1208, Germany) was transformed with the ligation mixture, and zeocin resistant clones were selected. Based on restriction analysis, a plasmid clone containing an insert of the expected size was retained for further characterization. Sequence determination of the vector pPICZα-KMPLGI (clone #3) confirmed the precise insertion of the amplified fragment fused to the α-factor mating signal, as well as the absence of unwanted mutations in the cloned region (the primers LY-MINPLGI and LY-MINPLG2 were used).

EXAMPLE 2

High Level Expression and Purification of Recombinant Human Microplasminogen: Quantitative Activation and Stabilization of Microplasmin 10 μg of the vector pPICZα-MPLG1 was digested with Pmel, which linearizes the vector in the 5' AOX1 region. The DNA was concentrated to about 0.33 μg/μl by precipitation, and 5 μl was used to transform competent *Pichia pastoris* X33 cells prepared according to the manual provided in the EasySelect Pichia expression kit.

The selection of a high-expression strain was performed as follows. Zeocin resistant transformants were selected on YPDSZ plates (1% yeast extract, 2% peptone, 2% glucose, 1M sorbitol, 2% agar, 100 μg/ml zeocin). Thirty-four single colonies were inoculated in 10 ml BMYZ-glycerol medium (1% yeast extract, 2°/peptone, 1% glycerol, 100 mM potassium phosphate, pH 6.0, 1.34% yeast nitrogen base, $4 \times 10^{-5}$% biotin, 100 μg/ml zeocin) in 50 ml Falcon tubes and cultured for 16 hours at 30° C. The cells were pelleted and re-sus-

```
LY-MINPLG1: 5' GGGGTATCT CTC GAG AAA AGA GCA CCT CCG CCT GTT   (SEQ.ID. No.9)
               GTC CTG CTT CC

LY-MINPLG2: 5' GCA GTG GGC TGC AGT CAA CAC CCA CTC              (SEQ.ID. No.10)
```

The LY-MINPLG1 primer has an annealing region corresponding to residues 444-452 of plasminogen (Ala-Pro-Pro-Pro-Val-Val-Leu-Leu-Pro) [SEQ ID. NO: 14] preceded by a pended in 2 ml of BMYZ-methanol medium (same as BMYZ-glycerol but with 0.5% methanol instead of glycerol) to induce expression from the AOX1 promoter, and cultured for 40 hours. 4 pulses of 0.5% methanol were regularly supplied to the cultures over this period. At the end of the induction culture, the presence of microplasminogen in the culture supernatant was estimated as described by Lijnen et al. in *Eur. J. Biochem.* (1981) 120:149. Briefly, the microplasminogen in pure or 10-fold diluted supernatants were incubated with urokinase for 30 minutes to activate microplasminogen in microplasmin. The generated microplasmin activity, as determined by its amidolytic activity measured with the chromogenic substrate S2403 (available from Chromogenix, Antwerp, Belgium) at different times, was compared to the activity of known amounts of purified plasmin or microplasmin preparations. The clone X33-MPLG1 #5, showing the highest microplasmin activity after urokinase activation, was selected for subsequent large scale production.

Fermentation of X33-MPLG1#5 at a 50 litre scale was carried out in four steps as follows. 2 l flask cell cultures were performed for 23 hours at 30° C. in 400 ml YSG+(yeast extract 6 g/l, soya peptone 5 g/l, glycerol 20 g/l) using an inoculum of 0.7 ml of cell bank (glycerol OOC17) and 270 rpm agitation, yielding (at the end of the pre-culture step) an OD600 of 15. Fermentation was then performed in a MRP80 fermentation device in 30 l basal medium (26.7 ml/l H3PO4 85%; 1.05 g/l CaSO4.2H2O, 18.2 g/l K2SO4, 14.9 g/l MgSO4.7H2O, 4.13 g/l KOH, 40 g/l glycerol 100% and 4.76 mill PTM1 salt solution [comprising 6 g/l CuSO4.5H2O, 0.08 g/l NaI, 3.36 g/l MnSO4.H2O, 0.2 g/l NaMoO4.2H2O, 0.02 g/l Boric acid, 0.82 g/l CoCl2.6H$_2$O, 20 g/l ZnCl2, 65 g/l FeSO4.7H2O, 0.2 g/l d-biotin and 5 ml/l HSSO4]), using 600 ml inoculum at 30° C. with an air flow of 50 l/min at atmospheric pressure, dissolved oxygen (DO)>20% and 200-500 rpm agitation, pH being maintained at 5.8 with 12.5% ammonia. At 24 hours and OD 600 of 50 (end of batch step), glycerol depletion was evidenced by a rapid increase of dissolved oxygen. Glycerol feeding (632 g/l glycerol 100% and 12 ml/l PTM1) increased the OD 600 up to 258 in 24 hours. Methanol feeding was then carried out with an increasing flow of up to 250 ml/h within 6 hours, which was maintained for 66 hours using 988 ml/l methanol and 12 ml/l PTM1 to reach an OD 600 of 352 at the end of culture. Fermentation of X33-MPLG1#5 at a 350 litre scale provided proportionally similar results.

The harvest was then purified in a three-steps process comprising cation exchange expanded bed chromatography, hydrophobic chromatography and affinity chromatography as follows:

a) Cation Exchange Expanded Bed Chromatography

Cation exchange expanded bed adsorption chromatography was conducted with Streamline SP (available from Pharmacia Biotechnology, Cat. No. 17-0993-01/02) packed in a Streamline 200 column (Pharmacia Biotechnology Cat No. 18-1100-22) with a bed volume of 5,120 cm$^3$, expanded and equilibrated by applying an upward flow of 1 M NaCl, 25 mM sodium acetate (CH$_3$COONa.3H$_2$O), buffer, pH 6.0, for two column volumes followed by column volumes of 25 mM sodium acetate buffer, pH 6.0. The fermentation broth was on line diluted (7x) with water and passed upwards through the expanded bed at a flow rate of 1000 ml/min. Loosely bound material was washed out with the upward flow of 25 mM sodium acetate buffer pH 6.0. The column adaptor was then lowered to the surface of the sedimented bed at a height of 16.3 cm. Flow was reversed and the captured proteins eluted with 2 column volumes of 0.5 M NaCl, 25 mM sodium acetate buffer, pH 6.0. Solid ammonium sulfate was added to the eluted Streamline fraction to reach 30% saturation (164 g ammonium sulfate per liter of eluted Streamline fraction) and the mixture was gently stirred at 4-8° C. for 1 hour.

b) Hydrophobic Chromatography

Hydrophobic chromatography was conducted with Hexyl TSK 650C (available from Toso-Haas Cat. No. 19027) packed in a Vantage 180/500 column (available from Millipore, Cat. No. 87018001) with a pack d volume of 2,700 cm$^3$ at 4-8° C. The eluted streamline fraction was loaded on the column at a flow rate of 38 l/hour. The column was then washed with 1.5 column volumes of 25 mM sodium acetate buffer, pH 6.0, containing 164 g/l ammonium sulfate and eluted from the column with 7 column volumes of 25 mM sodium acetate buffer, pH 6.0.

c) Affinity Chromatography

Affinity chromatography was conducted with Blue Sepharose 6 Fast Flow (available from Pharmacia Biotechnology, Cat. No. 17-0948-02/03) packed in a Vantage 130/500 column (available from Millipore, Cat. No. 87013001) with a packed volume of 3,186 cm3 at 4-8° C. The eluted fraction was loaded on the column at a flow rate of 20 l/hour, and washed with one column volume of 25 mM disodium hydrogenophosphate (Na$_2$HPO$_4$.12 H$_2$O) buffer, pH 7.0. The microplasminogen protein fraction was eluted from the column with 5 column volumes 0.5 M NaCl, 25 mM di-sodium hydrogenophosphate buffer, pH 7.0 and kept frozen at −20° C. The purity of the material was above 98% as demonstrated by SDS gel electrophoresis.

Quantitative Activation to and Stabilization of Microplasmin a) Quantitative Activation The activation of microplasminogen to microplasmin was performed at 23° C. for 30 minutes at a molar ratio of 0.5% of a staphylokinase variant SY162 in 0.5 M NaCl, 25 mM di-sodium hydrogenophosphate (Na$_2$HPO$_4$.12 H$_2$O) buffer, pH 7.0. SY162 is a staphylokinase variant with reduced immunogenicity comprising 12 amino-acid substitutions (K35A, E65Q, K74R, E80A, D82A, T90A, E99D, T101S, E108A, K109A, K130T and K135R) as compared to wild-type, as described by WO 99/40198. Solid ammonium sulfate was added to microplasmin at a final concentration of 1 M (132 g/l) and the mixture stirred at 4-8° C. for 15 minutes.

b) Hydrophobic Chromatography

Hydrophobic chromatography was conducted with Phenyl Sepharose 6 Fast Flow (available from Pharmacia Biotechnology, Cat. No. 17-0965-03/05) packed in a BPG 100/500 column (available from Pharmacia Biotechnology, Cat. No. 18-1103-01) having a packed volume of 1,738 cm$^3$, equilibrated with 4 column volumes of 25 mM Na$_2$HPO$_4$.12 H$_2$O buffer, pH 7.0, containing 0.1 M tranexamic acid (available from Boumonville Pharma, Braine-L'Alleud, Belgium) and 1 M (NH$_4$)$_2$SO4, pH 7.0, at 4-8° C. The activated product was loaded on the column at a linear flow rate of 18 l/hour and washed with 4.5 column volumes of 25 mM Na$_2$HPO$_4$.12 H$_2$O buffer, pH 7.0, containing 0.1 M tranexamic acid and 1 M (NH$_4$)$_2$SO$_4$. Microplasmin was eluted from the column at a linear flow rate of 6 l/hour with 5 column volumes of 25 mM Na$_2$HPO$_4$.12 H$_2$O buffer, pH 7.0, containing 0.1 M tranexamic acid and 0.7 M (NH$_4$)$_2$SO$_4$ and equilibrated with phosphate buffered saline containing 0.1 M tranexamic acid. Staphylokinase variant SY162 was eluted from the column with 25 mM Na$_2$HPO$_4$.12 H$_2$O buffer, pH 7.0 containing 0.1 M tranexamic acid. This procedure removed above 99% of staphylokinase from the microplasmin peak as demonstrated with a specific ELISA assay.

c) Concentration and Diafiltration by Tangential Ultrafiltration

Ultrafiltration was conducted with 2 Pellicon 2 Biomax membranes (5 kDa, 2.5 µm, available from Millipore, Bedford, Mass., Cat. n° P2B005A25) at 2-8° C. The membranes were mounted in a Pellicon 2 Process Holder connected to a Microgon pump Cart System (available from Microgon, Laguna Hills, Calif.). The membranes were washed with purified water and membrane integrity tested before operation. The sanitization was performed by continuous recirculation with 0.5 M NaOH for 60 minutes and with 0.1 M NaOH during 60 minutes. The membranes were then rinsed with 5 mM citric acid, pH 3.1, until the permeate reached a pH of 3.1. The pH of the Phenyl Sepharose eluate was adjusted to 3.1 and the protein was concentrated to 4 mg/ml by ultrafiltration. Diafiltration was performed for 60 to 90 minutes against 5 volumes of 5 mM citric acid, pH 3.1. Yields (expressed in grams) of three runs performed on a 50 litre fermentation apparatus are summariz d in the following Table 1 (ND : not determined).

TABLE 1

|  | Run 1 | Run 2 | Run 3 |
|---|---|---|---|
| Fermentor | 220 | 240 | ND |
| Streamline | 50 | 79 | 130 |
| Hexyl | 36 | 37 | ND |
| Blue | 25 | 28 | 30 |
| Phenyl | 17 | 20 | 26 |
| Diafiltration | — | — | 22 | d) Sterile Filtration (0.2 µm)

Mannitol was added at 2-8° C. to a concentration of 1.5 g/g of protein and sterile filtration performed at 23° C. on a Millipak 100 filter (size 500 cm$^2$) (available from Millipore, Cat. No. MPGL10CA3) and rinsed with about 500 ml of 5 mM citric acid, pH 3.1, with a peristaltic pump at a flow rate of 500 ml/minute. The filtrate was collected in a sterile and pyrogen free bag and stored at −20° C.

EXAMPLE 3

Expression of Recombinant Human Miniplasminogen

About 15 µg of the vector pPICZα-KMPLG1 was digested in a 20 µl reaction with PmeI, which linearizes the vector in the 5' AOX1 region. The linear DNA (3 µg) was used to transform competent *Pichia pastoris* X33 cells prepared according to the manual provided in the EasySelect *Pichia* Expression kit.

The selection of high-expression strain was performed essentially as follows. Zeocin resistant transformants were selected on YPDSZ plates (as defined in example 2). Fifty isolated colonies were inoculated in 15 ml BMYZ-glycerol medium (as d fined in example 2) in 50 ml Falcon tubes and cultured for 16 hours at 30° C. The cells were pelleted and re-suspended in 1.5 ml of BMYZ-methanol medium (as defined in example 2) to induce expression from the AOX1 promoter, and cultured for 40 hours. 3 or 4 pulses of 0.5% methanol were regularly supplied to the cultures over this period. At the end of the induction culture, the presence of miniplasminogen in the culture supernatant was estimated as described by Lijnen et al. (cited supra). Briefly, the miniplasminogen in 10-fold diluted supernatants were incubated with streptokinase for 10 minutes to form an active complex. The generated miniplasmin activity, as determined with the chromogenic substrate S2403 (see example 2) at different times, was compared to the activity of known amounts of a purified plasminogen preparation. In these conditions, all tested clones were producing miniplasminogen with yields varying between 3 and 15 mg/l. The two clones X33-KMPLG1 #6 and X33-KMPLG1 #25, showing the highest miniplasmin activity, were selected for subsequent large scale production.

EXAMPLE 4

Murine Cerebral Ischemic Infarction Model (General Procedure)

Experiments were conducted according to the guiding principles of the American Physiological Society and the International Committee on Thrombosis and Haemostasis as disclosed by Giles in Thromb. Haemost. (1987) 58:1078.

Focal cerebral ischemia was produced by persistent occlusion of the middle cerebral artery (hereinafter MCA) according to Welsh et al. in *J. Neurochem.* (1987) 49:846. Briefly, mice of either sex, weighing 20 to 30 g, were anesthetized by intraperitoneal injection of 75 mg/ml ketamine (available from Apharmo, Arnhem, The Netherlands) and 5 mg/ml xylazine (available from Bayer, Leverkusen, Germany). Alternatively, in order to ensure that these drugs did not affect cerebral infarct size, anesthesia was performed with inhalation of 2% isoflurane in oxygen. 1 mg/kg atropine (available from Federa, Brussels, Belgium) was administered intramuscularly, and rectal temperature was maintained at 37° C. by keeping the animals on a heating pad. A "U" shape incision was made between the left ar and left eye. The top and backside segments of the temporal muscle were transsected and the skull was exposed by retraction of the temporal muscle. A 1 mm diameter opening was made in the region ov r the MCA with a hand-held drill, with saline superfusion to prevent heat injury. The meninges were removed with a forceps and the MCA was occluded by ligation with a 10-0 nylon thread (available from Ethylon, Neuilly, France) and trans-sected distally to the ligation point. Finally the temporal muscle and skin were sutured back in place. The recombinant microplasmin produced in example 2 was then given intravenously as a bolus, 15 minutes after ligation of the MCA unless otherwise indicated. The animals were allowed to recover. After 24 hours, the animals were sacrificed with 500 mg/kg Nembutal (available from Abbott Laboratories, North Chicago, Ill.) and decapitated. The brain was removed and placed in a matrix for sectioning in 1 mm segments. The sections were immersed in 2% 2,3,5-triphenyltetrazolium chloride in saline, incubated for 30 minutes at 37° C., and placed in 4% formalin in phosphate buffered saline. With this procedure, the necrotic infarct area remains unstained and is clearly distinguishable from stained viable tissue. The sections were photographed and subjected to planimetry. The volume of the focal cerebral ischemic injury was defined as the sum of the unstained areas of the sections, multiplied by their thickness.

$\alpha_2$-Antiplasmin levels in murine plasma were measured by a chromogenic substrate assay, based on its rapid inhibition of plasmin, according to the procedure described by Edy et al. in Thromb. Res. (1976) 8:513. Briefly, 10 µl murine plasma (diluted 1/10 in 0.05 M NaH$_2$PO$_4$ buffer, pH 7.4, containing 0.01 percent Tween 20) was mixed at 37° C. with 420 µl 0.05 M Tris.HCl, 0.1 M NaCl buffer, pH 7.4, containing 0.01% Tween 20, and with 20 µl of 0.125 µM human plasmin (final concentration 5 nM). After 10 seconds incubation, 50 µ of 3 mM S2403 (Chromogenix, Antwerp, Belgium) was added and the change in absorbance measured at 405 nm. Changes in absorbance of 0.18 min$^{-1}$ for buffer and 0.09 min$^{-1}$ for pooled murine plasma were used for the construction of a calibration curve. Data are presented in tables 2a and 2b.

EXAMPLE 5

Effect of Recombinant Human Microplasmin on Cerebral Infarct Size In Mic

Effect of Recombinant Microplasmin on α-antiplasmin and Fibrinogen Levels

Effects of an intravenous bolus injection of the recombinant human microplasmin of example 2 in inbred BALB/c mice on plasma %-antiplasmin and fibrinogen levels are summarized in Table 2a. The $\alpha_2$-antiplasmin and fibrinogen levels decreased proportionally to the microplasmin dose and partially recovered within one hour, suggesting that $\alpha_2$-antiplasmin depletion was transient during the first few hours after the single bolus injection of microplasmin.

Effect of Recombinant Microplasmin on Cerebral Infarct Size

Ligation of the MCA induced a cerebral infarct with a volume of 29 μl in inbred BALB/c mice (Table 2b). Injection of 0.07 mg recombinant human microplasmin had no significant effect on infarct size, whereas injection of 0.13 mg microplasmin or more produced a significant reduction of cerebral infarct size. This is consistent with the above transient minor reduction of $\alpha_2$-antiplasmin with the lower dose and the more persistent depletion obtained with 0.2 mg microplasmin.

TABLE 2a

| Compound | Dose (mg) | Residual $\alpha_2$-antiplasmin (%) 15 min. | 1 h. | Residual Fibrinogen (%) 15 min. | 1 h. |
|---|---|---|---|---|---|
| Saline | — | 99 | — | 100 | — |
| Microplasmin | 0.07 | 58 | 75 | 93 | 79 |
|  | 0.13 | 14 | 44 | 33 | 17 |
|  | 0.20 | 0 | 18 | ND | ND |

ND: not determined

TABLE 2b

| Compound | Dose (mg) | Cerebral Infarct Size (mm$^3$) | p* |
|---|---|---|---|
| Saline | — | 29 (27-30) | — |
| Microplasmin | 0.07 | 29 (27-30) | 0.74 |
| id. | 0.13 | 26 (21-28) | 0.041 |
| id. | 0.13 + 0.07** | 26 (20-28) | 0.02 |

The data represent median and range of values obtained in 6 experiments
*versus saline
**injected 15' and 60' after MCA occlusion respectively

EXAMPLE 6

Rabbit Extracorporeal Loop Thrombolysis Model (General Procedure)

A simple extracorporeal loop thrombosis model in rabbits was used for the quantitative evaluation of the thrombolytic effect of human plasmin and microplasmin, as disclosed by Hotchkiss et al. in Thromb. Haemost. (1987) 58:107.

New Zealand white rabbits with a body weight of 2.6-3.2 kg were anesthesized by intramuscular injection of 1.0 of 2% xylazine and 0.5 ml of ketamine (same suppliers as in example 4). Additional Nembutal (12 mg/hour) was administered to maintain anesthesia. Thyroidal uptake of radioiodide was blocked by administration of sodium iodide (0.5 ml of a 2% solution). A femoral vein catheter was introduced for blood sampling and a femoral artery catheter for blood pressure measurement (PDCR 75 from Druck Ltd, Leicester, United Kingdom).

A 300 μl thrombus was formed around a woollen thread introduced longitudinally in each of two adapted insulin syringes from a mixture of 125I-labeled fibrinogen (approximately 400,000 cpm), platelet poor rabbit plasma, and 0.07 ml thrombin solution (100 NIH U/ml). In all instances, the clot formed quickly and was allowed to age for 30 minutes at 37° C. The two syringes were then inserted in an extracorporeal loop of silicon tubing between a femoral artery and a marginal ear vein. The blood flow was regulated via a peristaltic pump (P1 available from Pharmacia LKB, Piscataway, N.J.). Thrombotic extension of the clot was prevented by infusion of heparin (300 U/kg bolus followed by 200 U/kg over 2 hours) and the platelet aggregation inhibitor Ridogrel (7.5 mg/kg) bolus, 30 minutes before starting infusion of wild-type plasmin (available from Janssen Research Foundation, Beerse, Belgium) or the recombinant microplasmin obtained in example 2. The extent of thrombolysis was measured as the difference between the radioactivity introduced in the clot and that recovered in the syringes at the end of the experiment.

Local infusion was carried out by using a constant rate infusion pump (Perfuser VI, available from B. Braun, Penang, Malaysia), through a three-ways valve, in a volume of 6 ml over 2 hours proximal to the first inserted syringe in the extracorporal loop. The extent of thrombolysis was calculated 2.5 hours after starting infusion, as the difference between the radioactivity originally incorporated in the clot and the radioactivity in the syringe, and expressed as a percentage of the initial radioactivity.

2-ml blood samples were drawn into trisodium citrate (final concentration 0.011 M) before starting infusion and at hourly intervals for 2 hours. These samples were used for measurements of fibrinogen, ct-antiplasmin, and activated partial thromboplastin time. Bleeding times were performed by applying a Symplate II device (available from Organon Technica, Durham, N.C.) to a shaved inner thigh surface.

EXAMPLE 7

Effect of Recombinant Microplasmin on Extracorporeal Loop Clot Lysis

Results of the determinations made in accordance with the general procedure of example 6 are presented in the following Table 3. Clot lysis with the recombinant microplasmin of example 2 produced minor $\alpha_2$-antiplasmin depletion and fibrinogen breakdown and was associated with minor bleeding time prolongation. Infusion of wild-type plasmin resulted in a r duction of 80% of $\alpha_2$-antiplasmin and fibrinogen levels, with minor effect on the bleeding time. These findings indicate that the extent of clot lysis by recombinant microplasmin and wild-type plasmin is mainly determined by the dose of the drug and its delivery in the vicinity of the thrombus. Thrombolysis with recombinant microplasmin or wild-type plasmin thus was not associated with extensive systemic activation of the fibrinolytic system as evidenced by the moderate changes in fibrinogen, $\alpha_2$-antiplasmin and bleeding time.

TABLE 3

| Substance | Blood flow (ml/min) | Dose (mg/kg) | Clot Lysis (percent) | Residual Fibrinogen (percent)* | Residual α₂-antiplasmin (percent)* | Bleeding time (sec)* |
|---|---|---|---|---|---|---|
| Solvent | | — | 26 | 110 | 110 | 90 |
| Microplasmin | 0.5 | 0.6 | 43 | 93 | 97 | 95 |
| | | 1.3 | 46 | 93 | 96 | 145 |
| | | 2.5 | 51 | 79 | 71 | 120 |
| | | 3.8 | 64 | 77 | 71 | 150 |
| | | 5.0 | 60 | 67 | 67 | 90 |
| | 0.1 | 2.5 | 80 | 87 | 87 | 98 |
| Plasmin | 0.5 | 2.5 | 44 | 82 | 80 | 170 |
| | | 5.0 | 53 | 80 | 86 | 170 |
| | 0.1 | 2.5 | 56 | 93 | 120 | |

*at the end of the infusion.

EXAMPLE 8

Dog Circumflex Coronary Artery Copper Coil-Induced Thrombosis (General Procedure)

A copper coil was introduced in the coronary artery for the quantitative evaluation of the thrombolytic effect of human wild-type plasmin and recombinant microplasmin as described by Bergmann et al. in Science (1983) 220:1181-1183. Dogs were anesthesized by intravenous injection of 30 mg/kg Nembutal of after prem dication by intramuscular injection with atropine 12.5 µg/kg and ketamine 10 mg/kg (same suppliers as in example 4). Anesthesia was maintained by Nembutal infusion of 8 to 10 mg/kg/hour. After pre-medication, an intravenous line is introduced in the front leg vein and fix. This intravenous line is taken for anaesthetic drug administration and infusion. A second venous access line is introduced in a saphenous vein for heparin administration. During further preparation the line is kept open with a saline infusion at approx. 20 ml/hour. The femoral artery is exposed via an incision close to the groin and a catheter is introduced for blood sampling. The right and left carotid arteries are exposed for coronary catheterisation. ECG electrodes and a rectal temperature probe are placed for continuous monitoring of the ECG and the body temperature. The copper coil should be rinsed with 50% acetic acid to remove oxidation to have an optimal thrombogenic copper surface. A Lehman catheter (5 Fg, USCI Bard) is connected to the angiographic valve system introduced into the left carotid artery and advanced into the left coronary artery. An angiogram is performed to identify the position of the first major side branch of the circumflex artery. The angiographic valve system is disconnected and thin guide wire is introduced through the Lehman catheter and positioned distally to the first dominant side branch. The angiographic valve system should have the following connections: contrast medium, pressurized saline, pressure transducer (to monitor non occlusive catheter placement) and infusion line for intracoronary recombinant microplasmin administration. The Lehman catheter is retracted and removed, while the guidewire is kept in position. Over this guide wire the copper coil, fixed to a second guidewire is introduced and advanced into the circumflex artery and placed distally to the first dominant side branch. A selection of copper coils is available and the best estimated size used e.g. a 3-mm copper coil (six turns of a 0.5 mm copper wire). The coil must be distal from the predominant side branch if not fibrillation upon occlusion might occur. The central guide wire is removed. Via the right carotid artery the Lehman catheter is reintroduced to perform the angiograms throughout the remaining part of the study. The formation of a thrombotic occlusion is monitored by electrocardiographic measurements or by angiography via the right carotid artery. The occlusion was confirmed by angiography. The occlusion is aged for 60 minutes. An angiogram is then performed to confirm total occlusion of the artery and the Lehman catheter is left in place, proximal to the thrombus without occlusion of the circumflex coronary artery for administration of recombinant microplasmin and to perform the angiograms. Then a heparin 200 units/kg intravenous bolus followed by a 40 units/kg/hour infusion at 1 ml/min intravenous infusion throughout the experiment is given via the saphenous vein catheter. Five minutes after heparin bolus administration, a first bolus over 5 minutes of 40% of the recombinant microplasmin dose is administered intracoronary via the Lehman catheter. If occlusion persists after 15 minutes, as evidenced by angiography, the remaining 60% of the recombinant microplasmin dose will be infused intracoronary over 1 hour. Reperfusion and reocclusion are evaluated angiographically at 15 minutes intervals or whenever electrocardiographic signs suggestive for reperfusion or re-occlusion occurred. At the end of the experiment, the animals are killed by administering an overdose of pentobarbital (10 ml of 60 mg/ml intravenously). Six blood samples of 4.5 ml blood are taken 0.5 ml 3.8% trisodium citrate (final concentration 0.011 M) and kept on ice. The timing of the blood samples was baseline (after 45 minutes of stable occlusion, 2 minutes after heparin bolus but before recombinant microplasmin administration, 5 minutes after recombinant microplasmin bolus administration, at end of infusion and 120 minutes after the end of the infusion). These samples are centrifugated at 2000 rpm for 10 minutes at 4° C. The plasma is collected and frozen at −20° C. for determination of fibrinogen and α₂-antiplasmin according to Edy et al.(cited supra).

EXAMPLE 9

Figure 2:
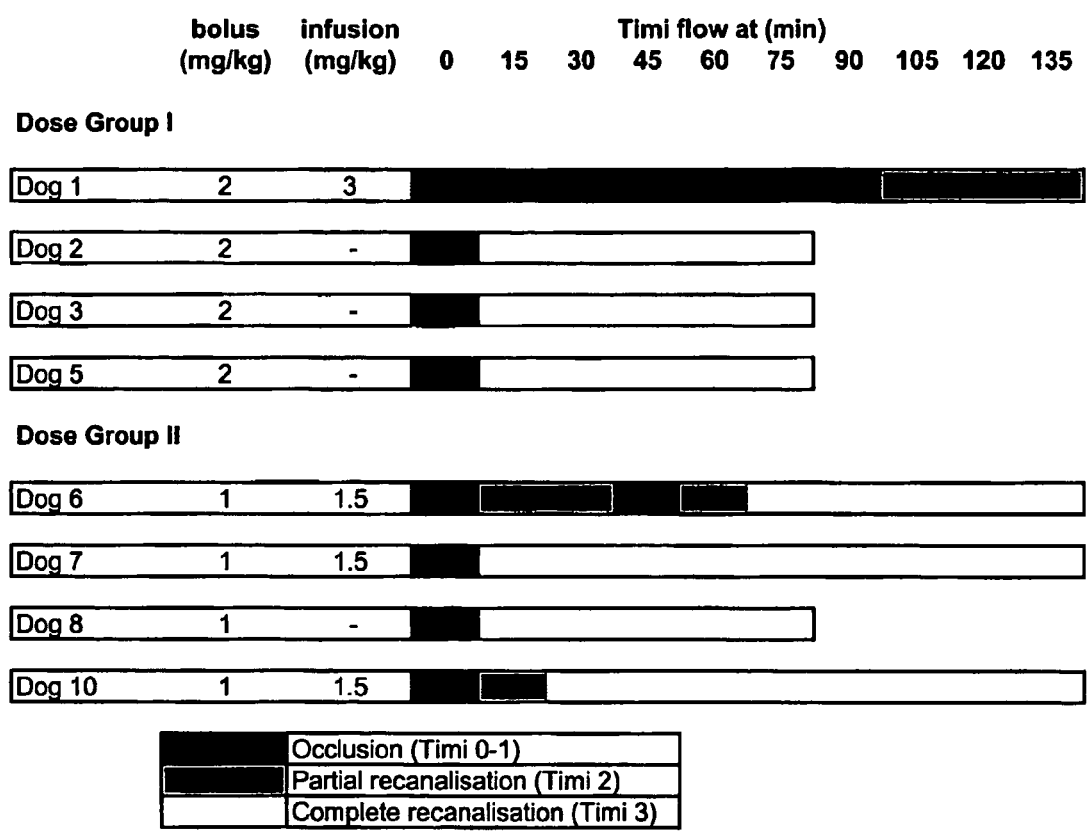
FIG. 2 shows individual data of angiographic examinations in dogs with a copper coil induced thrombosis after treatment with the recombinant microplasminogen of this invention.

Effect of Recombinant Microplasminogen on Copper-Coil Induced Myocardial Infarction Results of the determinations made in accordance with the general procedure of example 8 are presented in table 4 and FIG. 2. An erythrocyte-rich thrombus was formed within 15 minutes after introduction of the copper coil as evidenced electrocardiographic signs induced by the transmural ischemia and confirmed angiography via the right carotid artery. Two doses of the recombinant microplasminogen of example 2 were investigated in four animals per group. The first group received a bolus of 2 mg/kg over 5 minutes and, if occlusion persisted 15 minutes later as evidenced by angiography, a residual dose of 3 mg/kg was initiated over one hour. The second group received a bolus of 1 mg/kg and, if occlusion persisted 15 minutes later as evidenced by angiography, infusion of the residual 1.5 mg/kg was initiated over one hour.

In the first group, three dogs treated with the 2 mg/kg had a complete and persistent resolution of the thrombus within 15 minutes after administration. In the fourth dog, a complete and persistent partial recanalisation occurred after administration of the full dose (figure). In the second group, one dog had a complete and persistent reperfusion 15 minutes after bolus injection. In the remaining three dogs, the bolus followed by a 1 hour infusion of 1.5 m/kg induced a complete and persistent recanalisation (figure).

As shown in table 4, administration of recombinant microplasminogen induced only a partial decrease of fibrinogen and α2-antiplasmin.

TABLE 4

| Total Dose (mg/kg) | $\alpha_2$-antiplasmin (%) | | | | Fibrinogen (g/l) | | | |
|---|---|---|---|---|---|---|---|---|
| | Baseline | After heparin | 15 min after bolus | End of experiments | Baseline | After heparin | 15 min after bolus | End of experiments |
| 2 | 105 | 97 | 45 | 56 | 1.43 | 1.40 | 0.73 | 0.74 |
| 2.5 | 106 | 105 | 83 | 58 | 1.78 | 1.88 | 1.37 | 1.03 |

SEQUENCE LISTING

<160> NUMBER OF SEQ ID NOS: 10

<210> SEQ ID NO 1
<211> LENGTH: 2433
<212> TYPE: DNA
<213> ORGANISM: Homo sapiens
<220> FEATURE:
<221> NAME/KEY: CDS
<222> LOCATION: (1)...(2433)

<400> SEQUENCE: 1

```
atg gaa cat aag gaa gtg gtt ctt cta ctt ctt tta ttt ctg aaa tca         48
Met Glu His Lys Glu Val Val Leu Leu Leu Leu Leu Phe Leu Lys Ser
 1               5                  10                  15 ggt caa gga gag cct ctg gat gac tat gtg aat acc cag ggg gct tca         96
Gly Gln Gly Glu Pro Leu Asp Asp Tyr Val Asn Thr Gln Gly Ala Ser
             20                  25                  30 ctg ttc agt gtc act aag aag cag ctg gga gca gga agt ata gaa gaa        144
Leu Phe Ser Val Thr Lys Lys Gln Leu Gly Ala Gly Ser Ile Glu Glu
         35                  40                  45 tgt gca gca aaa tgt gag gag gac gaa gaa ttc acc tgc agg gca ttc        192
Cys Ala Ala Lys Cys Glu Glu Asp Glu Glu Phe Thr Cys Arg Ala Phe
     50                  55                  60 caa tat cac agt aaa gag caa caa tgt gtg ata atg gct gaa aac agg        240
Gln Tyr His Ser Lys Glu Gln Gln Cys Val Ile Met Ala Glu Asn Arg
 65                  70                  75                  80 aag tcc tcc ata atc att agg atg aga gat gta gtt tta ttt gaa aag        288
Lys Ser Ser Ile Ile Ile Arg Met Arg Asp Val Val Leu Phe Glu Lys
                 85                  90                  95 aaa gtg tat ctc tca gag tgc aag act ggg aat gga aag aac tac aga        336
Lys Val Tyr Leu Ser Glu Cys Lys Thr Gly Asn Gly Lys Asn Tyr Arg
            100                 105                 110 ggg acg atg tcc aaa aca aaa aat ggc atc acc tgt caa aaa tgg agt        384
Gly Thr Met Ser Lys Thr Lys Asn Gly Ile Thr Cys Gln Lys Trp Ser
        115                 120                 125 tcc act tct ccc cac aga cct aga ttc tca cct gct aca cac cca tca        432
Ser Thr Ser Pro His Arg Pro Arg Phe Ser Pro Ala Thr His Pro Ser
    130                 135                 140
```

-continued

| | |
|---|---|
| gag gga ctg gag gag aac tac tgc agg aat cca gac aac gat ccg cag<br>Glu Gly Leu Glu Glu Asn Tyr Cys Arg Asn Pro Asp Asn Asp Pro Gln<br>145                        150                     155                   160 | 480 |
| ggg ccc tgg tgc tat act act gat cca gaa aag aga tat gac tac tgc<br>Gly Pro Trp Cys Tyr Thr Thr Asp Pro Glu Lys Arg Tyr Asp Tyr Cys<br>                 165                     170                     175 | 528 |
| gac att ctt gag tgt gaa gag gaa tgt atg cat tgc agt gga gaa aac<br>Asp Ile Leu Glu Cys Glu Glu Glu Cys Met His Cys Ser Gly Glu Asn<br>        180                     185                     190 | 576 |
| tat gac ggc aaa att tcc aag acc atg tct gga ctg gaa tgc cag gcc<br>Tyr Asp Gly Lys Ile Ser Lys Thr Met Ser Gly Leu Glu Cys Gln Ala<br>            195                     200                     205 | 624 |
| tgg gac tct cag agc cca cac gct cat gga tac att cct tcc aaa ttt<br>Trp Asp Ser Gln Ser Pro His Ala His Gly Tyr Ile Pro Ser Lys Phe<br>210                     215                     220 | 672 |
| cca aac aag aac ctg aag aag aat tac tgt cgt aac ccc gat agg gag<br>Pro Asn Lys Asn Leu Lys Lys Asn Tyr Cys Arg Asn Pro Asp Arg Glu<br>225                        230                     235                   240 | 720 |
| ctg cgg cct tgg tgt ttc acc acc gac ccc aac aag cgc tgg gaa ctt<br>Leu Arg Pro Trp Cys Phe Thr Thr Asp Pro Asn Lys Arg Trp Glu Leu<br>                 245                     250                     255 | 768 |
| tgc gac atc ccc cgc tgc aca aca cct cca cca tct tct ggt ccc acc<br>Cys Asp Ile Pro Arg Cys Thr Thr Pro Pro Pro Ser Ser Gly Pro Thr<br>        260                     265                     270 | 816 |
| tac cag tgt ctg aag gga aca ggt gaa aac tat cgc ggg aat gtg gct<br>Tyr Gln Cys Leu Lys Gly Thr Gly Glu Asn Tyr Arg Gly Asn Val Ala<br>            275                     280                     285 | 864 |
| gtt acc gtt tcc ggg cac acc tgt cag cac tgg agt gca cag acc cct<br>Val Thr Val Ser Gly His Thr Cys Gln His Trp Ser Ala Gln Thr Pro<br>290                     295                     300 | 912 |
| cac aca cat aac agg aca cca gaa aac ttc ccc tgc aaa aat ttg gat<br>His Thr His Asn Arg Thr Pro Glu Asn Phe Pro Cys Lys Asn Leu Asp<br>305                     310                     315                   320 | 960 |
| gaa aac tac tgc cgc aat cct gac gga aaa agg gcc cca tgg tgc cat<br>Glu Asn Tyr Cys Arg Asn Pro Asp Gly Lys Arg Ala Pro Trp Cys His<br>                 325                     330                     335 | 1008 |
| aca acc aac agc caa gtg cgg tgg gag tac tgt aag ata ccg tcc tgt<br>Thr Thr Asn Ser Gln Val Arg Trp Glu Tyr Cys Lys Ile Pro Ser Cys<br>        340                     345                     350 | 1056 |
| gac tcc tcc cca gta tcc acg gaa caa ttg gct ccc aca gca cca cct<br>Asp Ser Ser Pro Val Ser Thr Glu Gln Leu Ala Pro Thr Ala Pro Pro<br>            355                     360                     365 | 1104 |
| gag cta acc cct gtg gtc cag gac tgc tac cat ggt gat gga cag agc<br>Glu Leu Thr Pro Val Val Gln Asp Cys Tyr His Gly Asp Gly Gln Ser<br>370                     375                     380 | 1152 |
| tac cga ggc aca tcc tcc acc acc acc aca gga aag aag tgt cag tct<br>Tyr Arg Gly Thr Ser Ser Thr Thr Thr Thr Gly Lys Lys Cys Gln Ser<br>385                     390                     395                   400 | 1200 |
| tgg tca tct atg aca cca cac cgg cac cag aag acc cca gaa aac tac<br>Trp Ser Ser Met Thr Pro His Arg His Gln Lys Thr Pro Glu Asn Tyr<br>                 405                     410                     415 | 1248 |
| cca aat gct ggc ctg aca atg aac tac tgc agg aat cca gat gcc gat<br>Pro Asn Ala Gly Leu Thr Met Asn Tyr Cys Arg Asn Pro Asp Ala Asp<br>        420                     425                     430 | 1296 |
| aaa ggc ccc tgt tgt ttt acc aca gac ccc agc gtc agg tgg gag tac<br>Lys Gly Pro Trp Cys Phe Thr Thr Asp Pro Ser Val Arg Trp Glu Tyr<br>            435                     440                     445 | 1344 |
| tgc aac ctg aaa aaa tgc tca gga aca gaa gcg agt gtt gta gca cct<br>Cys Asn Leu Lys Lys Cys Ser Gly Thr Glu Ala Ser Val Val Ala Pro<br>450                     455                     460 | 1392 |

```
ccg cct gtt gtc ctg ctt cca gat gta gag act cct tcc gaa gaa gac     1440
Pro Pro Val Val Leu Leu Pro Asp Val Glu Thr Pro Ser Glu Glu Asp
465                 470                 475                 480 tgt atg ttt ggg aat ggg aaa gga tac cga ggc aag agg gcg acc act     1488
Cys Met Phe Gly Asn Gly Lys Gly Tyr Arg Gly Lys Arg Ala Thr Thr
                    485                 490                 495 gtt act ggg acg cca tgc cag gac tgg gct gcc cag gag ccc cat aga     1536
Val Thr Gly Thr Pro Cys Gln Asp Trp Ala Ala Gln Glu Pro His Arg
                500                 505                 510 cac agc att ttc act cca gag aca aat cca cgg gcg ggt ctg gaa aaa     1584
His Ser Ile Phe Thr Pro Glu Thr Asn Pro Arg Ala Gly Leu Glu Lys
            515                 520                 525 aat tac tgc cgt aac cct gat ggt gat gta ggt ggt ccc tgg tgc tac     1632
Asn Tyr Cys Arg Asn Pro Asp Gly Asp Val Gly Gly Pro Trp Cys Tyr
530                 535                 540 acg aca aat cca aga aaa ctt tac gac tac tgt gat gtc cct cag tgt     1680
Thr Thr Asn Pro Arg Lys Leu Tyr Asp Tyr Cys Asp Val Pro Gln Cys
545                 550                 555                 560 gcg gcc cct tca ttt gat tgt ggg aag cct caa gtg gag ccg aag aaa     1728
Ala Ala Pro Ser Phe Asp Cys Gly Lys Pro Gln Val Glu Pro Lys Lys
                565                 570                 575 tgt cct gga agg gtt gtg ggg ggt gtg gcc cac cca cat tcc tgg         1776
Cys Pro Gly Arg Val Val Gly Gly Cys Val Ala His Pro His Ser Trp
                580                 585                 590 ccc tgg caa gtc agt ctt aga aca agg ttt gga atg cac ttc tgt gga    1824
Pro Trp Gln Val Ser Leu Arg Thr Arg Phe Gly Met His Phe Cys Gly
            595                 600                 605 ggc acc ttg ata tcc cca gag tgg gtg ttg act gct gcc cac tgc ttg    1872
Gly Thr Leu Ile Ser Pro Glu Trp Val Leu Thr Ala Ala His Cys Leu
        610                 615                 620 gag aag tcc cca agg cct tca tcc tac aag gtc atc ctg ggt gca cac    1920
Glu Lys Ser Pro Arg Pro Ser Ser Tyr Lys Val Ile Leu Gly Ala His
625                 630                 635                 640 caa gaa gtg aat ctc gaa ccg cat gtt cag gaa ata gaa gtg tct agg    1968
Gln Glu Val Asn Leu Glu Pro His Val Gln Glu Ile Glu Val Ser Arg
                645                 650                 655 ctg ttc ttg gag ccc aca cga aaa gat att gcc ttg cta aag cta agc    2016
Leu Phe Leu Glu Pro Thr Arg Lys Asp Ile Ala Leu Leu Lys Leu Ser
            660                 665                 670 agt cct gcc gtc atc act gac aaa gta atc cca gct tgt ctg cca tcc    2064
Ser Pro Ala Val Ile Thr Asp Lys Val Ile Pro Ala Cys Leu Pro Ser
        675                 680                 685 cca aat tat gtg gtc gct gac cgg acc gaa tgt ttc atc act ggc tgg    2112
Pro Asn Tyr Val Val Ala Asp Arg Thr Glu Cys Phe Ile Thr Gly Trp
690                 695                 700 gga gaa acc caa ggt act ttt gga gct ggc ctt ctc aag gaa gcc cag    2160
Gly Glu Thr Gln Gly Thr Phe Gly Ala Gly Leu Leu Lys Glu Ala Gln
705                 710                 715                 720 ctc cct gtg att gag aat aaa gtg tgc aat cgc tat gag ttt ctg aat    2208
Leu Pro Val Ile Glu Asn Lys Val Cys Asn Arg Tyr Glu Phe Leu Asn
                725                 730                 735 gga aga gtc caa tcc acc gaa ctc tgt gct ggg cat ttg gcc gga ggc    2256
Gly Arg Val Gln Ser Thr Glu Leu Cys Ala Gly His Leu Ala Gly Gly
            740                 745                 750 act gac agt tgc cag ggt gac agt gga ggt cct ctg gtt tgc ttc gag    2304
Thr Asp Ser Cys Gln Gly Asp Ser Gly Gly Pro Leu Val Cys Phe Glu
        755                 760                 765 aag gac aaa tac att tta caa gga gtc act tct tgg ggt ctt ggc tgt    2352
Lys Asp Lys Tyr Ile Leu Gln Gly Val Thr Ser Trp Gly Leu Gly Cys
770                 775                 780
```

```
gca cgc ccc aat aag cct ggt gtc tat gtt cgt gtt tca agg ttt gtt    2400
Ala Arg Pro Asn Lys Pro Gly Val Tyr Val Arg Val Ser Arg Phe Val
785             790                 795                 800 act tgg att gag gga gtg atg aga aat aat taa                        2433
Thr Trp Ile Glu Gly Val Met Arg Asn Asn *
            805                 810
```

<210> SEQ ID NO 2
<211> LENGTH: 810
<212> TYPE: PRT
<213> ORGANISM: Homo sapiens

<400> SEQUENCE: 2

```
Met Glu His Lys Glu Val Val Leu Leu Leu Leu Phe Leu Lys Ser
 1               5                  10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Pro Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335
```

```
Thr Thr Asn Ser Gln Val Arg Trp Glu Tyr Cys Lys Ile Pro Ser Cys
        340                 345                 350

Asp Ser Ser Pro Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415

Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
            435                 440                 445

Cys Asn Leu Lys Lys Cys Ser Gly Thr Glu Ala Ser Val Val Ala Pro
        450                 455                 460

Pro Pro Val Val Leu Leu Pro Asp Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
            515                 520                 525

Asn Tyr Cys Arg Asn Pro Asp Gly Asp Val Gly Gly Pro Trp Cys Tyr
        530                 535                 540

Thr Thr Asn Pro Arg Lys Leu Tyr Asp Tyr Cys Asp Val Pro Gln Cys
545                 550                 555                 560

Ala Ala Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Phe Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
            675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750
```

```
Thr Asp Ser Cys Gln Gly Asp Ser Gly Gly Pro Leu Val Cys Phe Glu
    755                 760                 765

Lys Asp Lys Tyr Ile Leu Gln Gly Val Thr Ser Trp Gly Leu Gly Cys
770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 3
<211> LENGTH: 750
<212> TYPE: DNA
<213> ORGANISM: Homo sapiens
<220> FEATURE:
<221> NAME/KEY: CDS
<222> LOCATION: (1)...(750)

<400> SEQUENCE: 3 gcc cct tca ttt gat tgt ggg aag cct caa gtg gag ccg aag aaa tgt        48
Ala Pro Ser Phe Asp Cys Gly Lys Pro Gln Val Glu Pro Lys Lys Cys
1               5                   10                  15 cct gga agg gtt gtg ggg ggg tgt gtg gcc cac cca cat tcc tgg ccc        96
Pro Gly Arg Val Val Gly Gly Cys Val Ala His Pro His Ser Trp Pro
            20                  25                  30 tgg caa gtc agt ctt aga aca agg ttt gga atg cac ttc tgt gga ggc       144
Trp Gln Val Ser Leu Arg Thr Arg Phe Gly Met His Phe Cys Gly Gly
        35                  40                  45 acc ttg ata tcc cca gag tgg gtg ttg act gct gcc cac tgc ttg gag       192
Thr Leu Ile Ser Pro Glu Trp Val Leu Thr Ala Ala His Cys Leu Glu
    50                  55                  60 aag tcc cca agg cct tca tcc tac aag gtc atc ctg ggt gca cac caa       240
Lys Ser Pro Arg Pro Ser Ser Tyr Lys Val Ile Leu Gly Ala His Gln
65                  70                  75                  80 gaa gtg aat ctc gaa ccg cat gtt cag gaa ata gaa gtg tct agg ctg       288
Glu Val Asn Leu Glu Pro His Val Gln Glu Ile Glu Val Ser Arg Leu
                85                  90                  95 ttc ttg gag ccc aca cga aaa gat att gcc ttg cta aag cta agc agt       336
Phe Leu Glu Pro Thr Arg Lys Asp Ile Ala Leu Leu Lys Leu Ser Ser
            100                 105                 110 cct gcc gtc atc act gac aaa gta atc cca gct tgt ctg cca tcc cca       384
Pro Ala Val Ile Thr Asp Lys Val Ile Pro Ala Cys Leu Pro Ser Pro
        115                 120                 125 aat tat gtg gtc gct gac cgg acc gaa tgt ttc atc act ggc tgg gga       432
Asn Tyr Val Val Ala Asp Arg Thr Glu Cys Phe Ile Thr Gly Trp Gly
    130                 135                 140 gaa acc caa ggt act ttt gga gct ggc ctt ctc aag gaa gcc cag ctc       480
Glu Thr Gln Gly Thr Phe Gly Ala Gly Leu Leu Lys Glu Ala Gln Leu
145                 150                 155                 160 cct gtg att gag aat aaa gtg tgc aat cgc tat gag ttt ctg aat gga       528
Pro Val Ile Glu Asn Lys Val Cys Asn Arg Tyr Glu Phe Leu Asn Gly
                165                 170                 175 aga gtc caa tcc acc gaa ctc tgt gct ggg cat ttg gcc gga ggc act       576
Arg Val Gln Ser Thr Glu Leu Cys Ala Gly His Leu Ala Gly Gly Thr
            180                 185                 190 gac agt tgc cag ggt gac agt gga ggt cct ctg gtt tgc ttc gag aag       624
Asp Ser Cys Gln Gly Asp Ser Gly Gly Pro Leu Val Cys Phe Glu Lys
        195                 200                 205 gac aaa tac att tta caa gga gtc act tct tgg ggt ctt ggc tgt gca       672
Asp Lys Tyr Ile Leu Gln Gly Val Thr Ser Trp Gly Leu Gly Cys Ala
    210                 215                 220
```

```
cgc ccc aat aag cct ggt gtc tat gtt cgt gtt tca agg ttt gtt act    720
Arg Pro Asn Lys Pro Gly Val Tyr Val Arg Val Ser Arg Phe Val Thr
225                 230                 235                 240 tgg att gag gga gtg atg aga aat aat taa                            750
Trp Ile Glu Gly Val Met Arg Asn Asn *
                245
```

<210> SEQ ID NO 4
<211> LENGTH: 249
<212> TYPE: PRT
<213> ORGANISM: Homo sapiens

<400> SEQUENCE: 4

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
            20                  25                  30

Trp Gln Val Ser Leu Arg Thr Arg Phe Gly Met His Phe Cys Gly Gly
        35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```

<210> SEQ ID NO 5
<211> LENGTH: 1047
<212> TYPE: DNA
<213> ORGANISM: Homo sapiens
<220> FEATURE:
<221> NAME/KEY: CDS
<222> LOCATION: (1)...(1047)

<400> SEQUENCE: 5

```
gca cct ccg cct gtt gtc ctg ctt cca gat gta gag act cct tcc gaa    48
Ala Pro Pro Pro Val Val Leu Leu Pro Asp Val Glu Thr Pro Ser Glu
1               5                   10                  15
```

```
gaa gac tgt atg ttt ggg aat ggg aaa gga tac cga ggc aag agg gcg      96
Glu Asp Cys Met Phe Gly Asn Gly Lys Gly Tyr Arg Gly Lys Arg Ala
         20                  25                  30 acc act gtt act ggg acg cca tgc cag gac tgg gct gcc cag gag ccc     144
Thr Thr Val Thr Gly Thr Pro Cys Gln Asp Trp Ala Ala Gln Glu Pro
             35                  40                  45 cat aga cac agc att ttc act cca gag aca aat cca cgg gcg ggt ctg     192
His Arg His Ser Ile Phe Thr Pro Glu Thr Asn Pro Arg Ala Gly Leu
     50                  55                  60 gaa aaa aat tac tgc cgt aac cct gat ggt gat gta ggt ggt ccc tgg     240
Glu Lys Asn Tyr Cys Arg Asn Pro Asp Gly Asp Val Gly Gly Pro Trp
 65                  70                  75                  80 tgc tac acg aca aat cca aga aaa ctt tac gac tac tgt gat gtc cct     288
Cys Tyr Thr Thr Asn Pro Arg Lys Leu Tyr Asp Tyr Cys Asp Val Pro
                 85                  90                  95 cag tgt gcg gcc cct tca ttt gat tgt ggg aag cct caa gtg gag ccg     336
Gln Cys Ala Ala Pro Ser Phe Asp Cys Gly Lys Pro Gln Val Glu Pro
            100                 105                 110 aag aaa tgt cct gga agg gtt gtg ggg ggg tgt gtg gcc cac cca cat     384
Lys Lys Cys Pro Gly Arg Val Val Gly Gly Cys Val Ala His Pro His
        115                 120                 125 tcc tgg ccc tgg caa gtc agt ctt aga aca agg ttt gga atg cac ttc     432
Ser Trp Pro Trp Gln Val Ser Leu Arg Thr Arg Phe Gly Met His Phe
    130                 135                 140 tgt gga ggc acc ttg ata tcc cca gag tgg gtg ttg act gct gcc cac     480
Cys Gly Gly Thr Leu Ile Ser Pro Glu Trp Val Leu Thr Ala Ala His
145                 150                 155                 160 tgc ttg gag aag tcc cca agg cct tca tcc tac aag gtc atc ctg ggt     528
Cys Leu Glu Lys Ser Pro Arg Pro Ser Ser Tyr Lys Val Ile Leu Gly
                165                 170                 175 gca cac caa gaa gtg aat ctc gaa ccg cat gtt cag gaa ata gaa gtg     576
Ala His Gln Glu Val Asn Leu Glu Pro His Val Gln Glu Ile Glu Val
            180                 185                 190 tct agg ctg ttc ttg gag ccc aca cga aaa gat att gcc ttg cta aag     624
Ser Arg Leu Phe Leu Glu Pro Thr Arg Lys Asp Ile Ala Leu Leu Lys
        195                 200                 205 cta agc agt cct gcc gtc atc act gac aaa gta atc cca gct tgt ctg     672
Leu Ser Ser Pro Ala Val Ile Thr Asp Lys Val Ile Pro Ala Cys Leu
    210                 215                 220 cca tcc cca aat tat gtg gtc gct gac cgg acc gaa tgt ttc atc act     720
Pro Ser Pro Asn Tyr Val Val Ala Asp Arg Thr Glu Cys Phe Ile Thr
225                 230                 235                 240 ggc tgg gga gaa acc caa ggt act ttt gga gct ggc ctt ctc aag gaa     768
Gly Trp Gly Glu Thr Gln Gly Thr Phe Gly Ala Gly Leu Leu Lys Glu
                245                 250                 255 gcc cag ctc cct gtg att gag aat aaa gtg tgc aat cgc tat gag ttt     816
Ala Gln Leu Pro Val Ile Glu Asn Lys Val Cys Asn Arg Tyr Glu Phe
            260                 265                 270 ctg aat gga aga gtc caa tcc acc gaa ctc tgt gct ggg cat ttg gcc     864
Leu Asn Gly Arg Val Gln Ser Thr Glu Leu Cys Ala Gly His Leu Ala
        275                 280                 285 gga ggc act gac agt tgc cag ggt gac agt gga ggt cct ctg gtt tgc     912
Gly Gly Thr Asp Ser Cys Gln Gly Asp Ser Gly Gly Pro Leu Val Cys
    290                 295                 300 ttc gag aag gac aaa tac att tta caa gga gtc act tct tgg ggt ctt     960
Phe Glu Lys Asp Lys Tyr Ile Leu Gln Gly Val Thr Ser Trp Gly Leu
305                 310                 315                 320 ggc tgt gca cgc ccc aat aag cct ggt gtc tat gtt cgt gtt tca agg    1008
Gly Cys Ala Arg Pro Asn Lys Pro Gly Val Tyr Val Arg Val Ser Arg
                325                 330                 335
```

```
ttt gtt act tgg att gag gga gtg atg aga aat aat taa                    1047
Phe Val Thr Trp Ile Glu Gly Val Met Arg Asn Asn *
    340                 345
```

<210> SEQ ID NO 6
<211> LENGTH: 348
<212> TYPE: PRT
<213> ORGANISM: Homo sapiens

<400> SEQUENCE: 6

```
Ala Pro Pro Val Val Leu Leu Pro Asp Val Glu Thr Pro Ser Glu
 1               5                  10                  15

Glu Asp Cys Met Phe Gly Asn Gly Lys Gly Tyr Arg Gly Lys Arg Ala
                20                  25                  30

Thr Thr Val Thr Gly Thr Pro Cys Gln Asp Trp Ala Ala Gln Glu Pro
            35                  40                  45

His Arg His Ser Ile Phe Thr Pro Glu Thr Asn Pro Arg Ala Gly Leu
        50                  55                  60

Glu Lys Asn Tyr Cys Arg Asn Pro Asp Gly Asp Val Gly Gly Pro Trp
65                  70                  75                  80

Cys Tyr Thr Thr Asn Pro Arg Lys Leu Tyr Asp Tyr Cys Asp Val Pro
                85                  90                  95

Gln Cys Ala Ala Pro Ser Phe Asp Cys Gly Lys Pro Gln Val Glu Pro
            100                 105                 110

Lys Lys Cys Pro Gly Arg Val Val Gly Gly Cys Val Ala His Pro His
        115                 120                 125

Ser Trp Pro Trp Gln Val Ser Leu Arg Thr Arg Phe Gly Met His Phe
    130                 135                 140

Cys Gly Gly Thr Leu Ile Ser Pro Glu Trp Val Leu Thr Ala Ala His
145                 150                 155                 160

Cys Leu Glu Lys Ser Pro Arg Pro Ser Ser Tyr Lys Val Ile Leu Gly
                165                 170                 175

Ala His Gln Glu Val Asn Leu Glu Pro His Val Gln Glu Ile Glu Val
            180                 185                 190

Ser Arg Leu Phe Leu Glu Pro Thr Arg Lys Asp Ile Ala Leu Leu Lys
        195                 200                 205

Leu Ser Ser Pro Ala Val Ile Thr Asp Lys Val Ile Pro Ala Cys Leu
    210                 215                 220

Pro Ser Pro Asn Tyr Val Val Ala Asp Arg Thr Glu Cys Phe Ile Thr
225                 230                 235                 240

Gly Trp Gly Glu Thr Gln Gly Thr Phe Gly Ala Gly Leu Leu Lys Glu
                245                 250                 255

Ala Gln Leu Pro Val Ile Glu Asn Lys Val Cys Asn Arg Tyr Glu Phe
            260                 265                 270

Leu Asn Gly Arg Val Gln Ser Thr Glu Leu Cys Ala Gly His Leu Ala
        275                 280                 285

Gly Gly Thr Asp Ser Cys Gln Gly Asp Ser Gly Gly Pro Leu Val Cys
    290                 295                 300

Phe Glu Lys Asp Lys Tyr Ile Leu Gln Gly Val Thr Ser Trp Gly Leu
305                 310                 315                 320

Gly Cys Ala Arg Pro Asn Lys Pro Gly Val Tyr Val Arg Val Ser Arg
                325                 330                 335

Phe Val Thr Trp Ile Glu Gly Val Met Arg Asn Asn
            340                 345
```

-continued

```
<210> SEQ ID NO 7
<211> LENGTH: 38
<212> TYPE: DNA
<213> ORGANISM: Homo sapiens
<220> FEATURE:
<221> NAME/KEY: misc_feature
<222> LOCATION: (1)...(38)

<400> SEQUENCE: 7
ggggtatctc tcgagaaaag agccccttca tttgattg                              38

<210> SEQ ID NO 8
<211> LENGTH: 38
<212> TYPE: DNA
<213> ORGANISM: Homo sapiens
<220> FEATURE:
<221> NAME/KEY: misc_feature
<222> LOCATION: (1)...(38)
<223> OTHER INFORMATION: reverse primer human microplasminogen

<400> SEQUENCE: 8
gtttttgttc tagattaatt atttctcatc actccctc                              38

<210> SEQ ID NO 9
<211> LENGTH: 47
<212> TYPE: DNA
<213> ORGANISM: Homo sapiens
<220> FEATURE:
<221> NAME/KEY: misc_feature
<222> LOCATION: (1)...(47)
<223> OTHER INFORMATION: foward primer human miniplasminogen

<400> SEQUENCE: 9
ggggtatctc tcgagaaaag agcacctccg cctgttgtcc tgcttcc                    47

<210> SEQ ID NO 10
<211> LENGTH: 27
<212> TYPE: DNA
<213> ORGANISM: Homo sapiens
<220> FEATURE:
<221> NAME/KEY: misc_feature
<222> LOCATION: (1)...(27)
<223> OTHER INFORMATION: reverse primer human miniplasminogen

<400> SEQUENCE: 10
gcagtgggct gcagtcaaca cccactc                                          27
```

The invention claimed is:

1. A yeast cell expressing microplasminogen encoded by a mammalian nucleotide sequence, wherein the amino acid sequence of said microplasminogen consists of the amino acid sequence of SEQ ID NO: 4.

2. The yeast cell according to claim 1, wherein said mammalian nucleotide sequence is the nucleotide sequence of SEQ ID NO: 3.

3. The yeast cell according to claim 1, wherein said mammalian nucleotide sequence is under the control of an inducible promoter.

4. The yeast cell according to claim 1, said yeast cell belonging to the group of the methylotrophic yeasts.

5. The yeast cell according to claim 4, wherein said yeast is selected from the group consisting of the *Hansenula, Pichia, Candida* and *Torulopsis genera*.

6. The yeast cell according to claim 4, belonging to the *Pichia pastoris* species.

7. The yeast cell according to claim 1, wherein said mammalian nucleotide sequence is integrated into the genome of said yeast cell.

8. The yeast cell according to claim 1, wherein said yeast cell is the deposited cell line with accession number MUCL43676.

9. The yeast cell according to claim 1, expressing said microplasminogen at a level of at least about 100 mg/litre.

10. The yeast cell according to claim 1, wherein said mammalian nucleotide sequence is fused to a nucleotide sequence encoding a secretion signal.

11. A yeast cell expressing microplasminogen, wherein the amino acid sequence of said microplasminogen consists of the amino acid sequence of SEQ ID NO: 4.

12. A method of producing activated microplasmin, said method comprising the steps of:
 (a) providing a yeast cell that is transformed with a nucleotide sequence encoding a microplasminogen amino acid sequence consisting of the amino acid sequence of SEQ ID NO: 4;

(b) culturing said yeast cell under conditions such that a microplasminogen consisting of said amino acid sequence is expressed; and (c) activating said microplasminogen by means of a plasminogen activator.

13. The method according to claim 12, wherein said plasminogen activator is staphylokinase.

14. The method according to claim 12, further comprising the step of stabilizing the expressed and activated microplasmin by means of a stabilizing agent or medium.

15. The method according to claim 14, wherein said stabilizing agent comprises an amino-acid selected from the group consisting of lysine, 6-amino hexanoic acid and tranexamic acid.

16. The method according to claim 14, wherein said stabilizing medium is an acid solution or an acid buffer.

17. The method according to claim 16, wherein said stabilizing medium is a citrate buffer with a pH of about 3.1.

18. The method according to claim 14, further comprising the step of drying the expressed, activated and stabilized microplasmin.

19. A recombinant mammalian protein obtained by the method according to claim 12.

20. The method according to claim 12, wherein said yeast cell is transformed with the nucleotide sequence of SEQ ID NO: 3 and a high expression *Pichia* strain of microplasminogen is selected.

21. The method according to claim 12, which optionally comprises the step of purifying said expressed microplasminogen obtained in step (b) by one or more purification methods.

22. The method according to claim 12 wherein said yeast cell is the deposited strain with accession number MUCL43676.

23. The method according to claim 12, wherein said microplasminogen is expressed at a level of about 100 mg/litre.

24. An isolated nucleotide sequence encoding a fusion protein of microplasminogen and a secretion signal sequence, wherein the amino acid sequence of said microplasminogen consists of the amino acid sequence of SEQ ID NO: 4.

25. The isolated nucleotide sequence of claim 24, said nucleotide sequence comprising the nucleotide sequence of SEQ ID NO: 3.

26. An isolated cell containing the nucleic acid molecule of claim 24.

27. An isolated vector containing the nucleic acid molecule of claim 24.

28. An isolated cell containing the vector of claim 27.

29. A purified microplasminogen, wherein the amino acid sequence of said microplasminogen consists of the amino acid sequence of SEQ ID NO: 4.

30. An isolated cell producing the microplasminogen of claim 29.

31. A pharmaceutical composition comprising microplasminogen, wherein the amino acid sequence of said microplasminogen consists of the amino acid sequence of SEQ ID NO: 4.

32. The pharmaceutical composition of claim 31, further comprising a pharmaceutically-acceptable carrier.

* * * * *

UNITED STATES PATENT AND TRADEMARK OFFICE
CERTIFICATE OF CORRECTION

PATENT NO.       : 7,445,775 B2                                       Page 1 of 1
APPLICATION NO.  : 10/450976
DATED            : November 4, 2008
INVENTOR(S)      : Collen et al.

It is certified that error appears in the above-identified patent and that said Letters Patent is hereby corrected as shown below:

On the title page,

[*] Notice:    Subject to any disclaimer, the term of this patent is extended or adjusted under 35 USC 154(b) by (386) days Delete the phrase "by 386 days" and insert -- by 556 days --

Signed and Sealed this

Twenty-second Day of December, 2009

David J. Kappos
*Director of the United States Patent and Trademark Office*

UNITED STATES PATENT AND TRADEMARK OFFICE
CERTIFICATE OF CORRECTION

PATENT NO.       : 7,445,775 B2                                              Page 1 of 26
APPLICATION NO.  : 10/450976
DATED            : November 4, 2008
INVENTOR(S)      : Collen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1045 days.

On the title page, item [56]: Under "References Cited," Under "OTHER PUBLICATIONS," insert --English translation of Office Action as issued by Japan Patent Office dated April 30, 2008 in Patent Application No. 067213/2007.--.

Column 2, Line 42, replace "factor XII." with --factor XIII.--.

Column 7,
  Line 1, delete "Insert the enclosed sequence listing at the end of the specification."
  Line 18, replace "th genome." with --the genome.--.
  Line 56, replace "m thod" with --method--.

Column 9,
  Line 31, replace "a factor" with --α factor--.
  Line 32, replace "wel" with --well--.

Column 11,
  Line 17, replace "2 I" with --2 l--.
  Line 23, replace "30 I" with --30 l--.
  Line 26, replace "mill" with --ml/l--.

Column 12,
  Line 7, replace "pack d" with --packed--.
  Line 53, replace "Boumonville" with --Bournonville--.

Signed and Sealed this

Thirtieth Day of November, 2010

David J. Kappos
*Director of the United States Patent and Trademark Office*

Column 13,
> Line 19, replace "summariz d" with --summarized--.
> Line 56, replace "d fined" with --defined--.

Column 14,
> Line 31, replace "left ar" with --left ear--.
> Line 34, replace "ov r" with --over--.

Column 15, Line 13, replace "%-antiplasmin" with --$\alpha_2$-antiplasmin--.

Column 16,
> Line 43, replace "ct-antiplasmin" with --$\alpha_2$-antiplasmin--.
> Line 59, replace "r duction" with --reduction--.

Column 17,
> In TABLE 3, under Column "Residual $\alpha_2$-antiplasmin
>   (percent)*," in bottom row, delete value "120".
> In TABLE 3, under Column "Bleeding time (sec)*," in bottom
>   row, insert value --120--.
> Line 29, replace "prem dication" with --premedication--.

Column 20, Line 5, replace "1.5 m/kg" with --1.5 mg/kg--.

Please replace the Sequence Listing in the above-referenced patent, from column 19 to column 38, with the Sequence Listing provided below.

```
SEQUENCE LISTING

<110>  Collen, Desire Jose
          Nagai, Nubuo
          Laroche, Yves

<120>  Yeast Expression Vector and a Method of Making a Recombinant
          Protein by Expression in a Yeast Cell

<130>  50304/005001

<140>  US 10/450,976
   <141>  2003-12-08

<150>  PCT/BE01/00217
   <151>  2001-12-20

<150>  GB 0116702
   <151>  2001-07-09

<150>  GB 0116690
   <151>  2001-07-09

<150>  GB 0031196
   <151>  2000-12-21

<160>  15

<170>  PatentIn version 3.3

<210>  1
   <211>  2433
```

<212> DNA
<213> Homo sapiens

<220>
<221> CDS
<222> (1)..(2433)

<400> 1

| | | | | | | | | | | | | | | | | |
|---|---|---|---|---|---|---|---|---|---|---|---|---|---|---|---|---|
| atg | gaa | cat | aag | gaa | gtg | gtt | ctt | cta | ctt | ctt | tta | ttt | ctg | aaa | tca | 48 |
| Met | Glu | His | Lys | Glu | Val | Val | Leu | Leu | Leu | Leu | Phe | Leu | Lys | Ser | | |
| 1 | | | | 5 | | | | | 10 | | | | | 15 | | |
| ggt | caa | gga | gag | cct | ctg | gat | gac | tat | gtg | aat | acc | cag | ggg | gct | tca | 96 |
| Gly | Gln | Gly | Glu | Pro | Leu | Asp | Asp | Tyr | Val | Asn | Thr | Gln | Gly | Ala | Ser | |
| | | | 20 | | | | | 25 | | | | | 30 | | | |
| ctg | ttc | agt | gtc | act | aag | aag | cag | ctg | gga | gca | gga | agt | ata | gaa | gaa | 144 |
| Leu | Phe | Ser | Val | Thr | Lys | Lys | Gln | Leu | Gly | Ala | Gly | Ser | Ile | Glu | Glu | |
| | | 35 | | | | | 40 | | | | | 45 | | | | |
| tgt | gca | gca | aaa | tgt | gag | gag | gac | gaa | gaa | ttc | acc | tgc | agg | gca | ttc | 192 |
| Cys | Ala | Ala | Lys | Cys | Glu | Glu | Asp | Glu | Glu | Phe | Thr | Cys | Arg | Ala | Phe | |
| 50 | | | | | 55 | | | | | 60 | | | | | | |
| caa | tat | cac | agt | aaa | gag | caa | caa | tgt | gtg | ata | atg | gct | gaa | aac | agg | 240 |
| Gln | Tyr | His | Ser | Lys | Glu | Gln | Gln | Cys | Val | Ile | Met | Ala | Glu | Asn | Arg | |
| 65 | | | | 70 | | | | | 75 | | | | | 80 | | |
| aag | tcc | tcc | ata | atc | att | agg | atg | aga | gat | gta | gtt | tta | ttt | gaa | aag | 288 |
| Lys | Ser | Ser | Ile | Ile | Ile | Arg | Met | Arg | Asp | Val | Val | Leu | Phe | Glu | Lys | |
| | | | 85 | | | | | 90 | | | | | 95 | | | |
| aaa | gtg | tat | ctc | tca | gag | tgc | aag | act | ggg | aat | gga | aag | aac | tac | aga | 336 |
| Lys | Val | Tyr | Leu | Ser | Glu | Cys | Lys | Thr | Gly | Asn | Gly | Lys | Asn | Tyr | Arg | |
| | | | 100 | | | | | 105 | | | | | 110 | | | |

```
ggg acg atg tcc aaa aca aaa aat ggc atc acc tgt caa aaa tgg agt        384
Gly Thr Met Ser Lys Thr Lys Asn Gly Ile Thr Cys Gln Lys Trp Ser
        115                 120                 125 tcc act tct ccc cac aga cct aga ttc tca cct gct aca cac ccc tca        432
Ser Thr Ser Pro His Arg Pro Arg Phe Ser Pro Ala Thr His Pro Ser
    130                 135                 140 gag gga ctg gag gag aac tac tgc agg aat cca gac aac gat ccg cag        480
Glu Gly Leu Glu Glu Asn Tyr Cys Arg Asn Pro Asp Asn Asp Pro Gln
145                 150                 155                 160 ggg ccc tgg tgc tat act act gat cca gaa aag aga tat gac tac tgc        528
Gly Pro Trp Cys Tyr Thr Thr Asp Pro Glu Lys Arg Tyr Asp Tyr Cys
                165                 170                 175 gac att ctt gag tgt gaa gag gaa tgt atg cat tgc agt gga gaa aac        576
Asp Ile Leu Glu Cys Glu Glu Glu Cys Met His Cys Ser Gly Glu Asn
            180                 185                 190 tat gac ggc aaa att tcc aag acc atg tct gga ctg gaa tgc cag gcc        624
Tyr Asp Gly Lys Ile Ser Lys Thr Met Ser Gly Leu Glu Cys Gln Ala
        195                 200                 205 tgg gac tct cag agc cca cac gct cat gga tac att cct tcc aaa ttt        672
Trp Asp Ser Gln Ser Pro His Ala His Gly Tyr Ile Pro Ser Lys Phe
    210                 215                 220 cca aac aag aac ctg aag aag aat tac tgt cgt aac ccc gat agg gag        720
Pro Asn Lys Asn Leu Lys Lys Asn Tyr Cys Arg Asn Pro Asp Arg Glu
225                 230                 235                 240 ctg cgg cct tgg tgt ttc acc acc gac ccc aac aag cgc tgg gaa ctt        768
Leu Arg Pro Trp Cys Phe Thr Thr Asp Pro Asn Lys Arg Trp Glu Leu
                245                 250                 255
```

| | | | | | | | | | | | | | | | | |
|---|---|---|---|---|---|---|---|---|---|---|---|---|---|---|---|---|
| tgc | gac | atc | ccc | cgc | tgc | aca | aca | cct | cca | cca | tct | tct | ggt | ccc | acc | 816 |
| Cys | Asp | Ile | Pro | Arg | Cys | Thr | Thr | Pro | Pro | Pro | Ser | Ser | Gly | Pro | Thr | |
| | | | 260 | | | | 265 | | | | | 270 | | | | |
| tac | cag | tgt | ctg | aag | gga | aca | ggt | gaa | aac | tat | cgc | ggg | aat | gtg | gct | 864 |
| Tyr | Gln | Cys | Leu | Lys | Gly | Thr | Gly | Glu | Asn | Tyr | Arg | Gly | Asn | Val | Ala | |
| | | 275 | | | | 280 | | | | | 285 | | | | | |
| gtt | acc | gtt | tcc | ggg | cac | acc | tgt | cag | cac | tgg | agt | gca | cag | acc | cct | 912 |
| Val | Thr | Val | Ser | Gly | His | Thr | Cys | Gln | His | Trp | Ser | Ala | Gln | Thr | Pro | |
| | 290 | | | | | 295 | | | | | 300 | | | | | |
| cac | aca | cat | aac | agg | aca | cca | gaa | aac | ttc | ccc | tgc | aaa | aat | ttg | gat | 960 |
| His | Thr | His | Asn | Arg | Thr | Pro | Glu | Asn | Phe | Pro | Cys | Lys | Asn | Leu | Asp | |
| 305 | | | | | 310 | | | | | 315 | | | | | 320 | |
| gaa | aac | tac | tgc | cgc | aat | cct | gac | gga | aaa | agg | gcc | cca | tgg | tgc | cat | 1008 |
| Glu | Asn | Tyr | Cys | Arg | Asn | Pro | Asp | Gly | Lys | Arg | Ala | Pro | Trp | Cys | His | |
| | | | | 325 | | | | | 330 | | | | | 335 | | |
| aca | acc | aac | agc | caa | gtg | cgg | tgg | gag | tac | tgt | aag | ata | ccg | tcc | tgt | 1056 |
| Thr | Thr | Asn | Ser | Gln | Val | Arg | Trp | Glu | Tyr | Cys | Lys | Ile | Pro | Ser | Cys | |
| | | | 340 | | | | | 345 | | | | | 350 | | | |
| gac | tcc | tcc | cca | gta | tcc | acg | gaa | caa | ttg | gct | ccc | aca | gca | cca | cct | 1104 |
| Asp | Ser | Ser | Pro | Val | Ser | Thr | Glu | Gln | Leu | Ala | Pro | Thr | Ala | Pro | Pro | |
| | | 355 | | | | | 360 | | | | | 365 | | | | |
| gag | cta | acc | cct | gtg | gtc | cag | gac | tgc | tac | cat | ggt | gat | gga | cag | agc | 1152 |
| Glu | Leu | Thr | Pro | Val | Val | Gln | Asp | Cys | Tyr | His | Gly | Asp | Gly | Gln | Ser | |
| | 370 | | | | | 375 | | | | | 380 | | | | | |
| tac | cga | ggc | aca | tcc | tcc | acc | acc | acc | aca | gga | aag | aag | tgt | cag | tct | 1200 |
| Tyr | Arg | Gly | Thr | Ser | Ser | Thr | Thr | Thr | Thr | Gly | Lys | Lys | Cys | Gln | Ser | |
| 385 | | | | | 390 | | | | | 395 | | | | | 400 | |

```
tgg tca tct atg aca cca cac cgg cac cag aag acc cca gaa aac tac    1248
Trp Ser Ser Met Thr Pro His Arg His Gln Lys Thr Pro Glu Asn Tyr
            405                 410                 415 cca aat gct ggc ctg aca atg aac tac tgc agg aat cca gat gcc gat    1296
Pro Asn Ala Gly Leu Thr Met Asn Tyr Cys Arg Asn Pro Asp Ala Asp
            420                 425                 430 aaa ggc ccc tgg tgt ttt acc aca gac ccc agc gtc agg tgg gag tac    1344
Lys Gly Pro Trp Cys Phe Thr Thr Asp Pro Ser Val Arg Trp Glu Tyr
            435                 440                 445 tgc aac ctg aaa aaa tgc tca gga aca gaa gcg agt gtt gta gca cct    1392
Cys Asn Leu Lys Lys Cys Ser Gly Thr Glu Ala Ser Val Val Ala Pro
450                 455                 460 ccg cct gtt gtc ctg ctt cca gat gta gag act cct tcc gaa gaa gac    1440
Pro Pro Val Val Leu Leu Pro Asp Val Glu Thr Pro Ser Glu Glu Asp
465                 470                 475                 480 tgt atg ttt ggg aat ggg aaa gga tac cga ggc aag agg gcg acc act    1488
Cys Met Phe Gly Asn Gly Lys Gly Tyr Arg Gly Lys Arg Ala Thr Thr
            485                 490                 495 gtt act ggg acg cca tgc cag gac tgg gct gcc cag gag ccc cat aga    1536
Val Thr Gly Thr Pro Cys Gln Asp Trp Ala Ala Gln Glu Pro His Arg
            500                 505                 510 cac agc att ttc act cca gag aca aat cca cgg gcg ggt ctg gaa aaa    1584
His Ser Ile Phe Thr Pro Glu Thr Asn Pro Arg Ala Gly Leu Glu Lys
            515                 520                 525 aat tac tgc cgt aac cct gat ggt gat gta ggt ggt ccc tgg tgc tac    1632
Asn Tyr Cys Arg Asn Pro Asp Gly Asp Val Gly Gly Pro Trp Cys Tyr
530                 535                 540
```

```
acg aca aat cca aga aaa ctt tac gac tac tgt gat gtc cct cag tgt      1680
Thr Thr Asn Pro Arg Lys Leu Tyr Asp Tyr Cys Asp Val Pro Gln Cys
545                 550                 555                 560 gcg gcc cct tca ttt gat tgt ggg aag cct caa gtg gag ccg aag aaa      1728
Ala Ala Pro Ser Phe Asp Cys Gly Lys Pro Gln Val Glu Pro Lys Lys
                565                 570                 575 tgt cct gga agg gtt gtg ggg ggg tgt gtg gcc cac cca cat tcc tgg      1776
Cys Pro Gly Arg Val Val Gly Gly Cys Val Ala His Pro His Ser Trp
            580                 585                 590 ccc tgg caa gtc agt ctt aga aca agg ttt gga atg cac ttc tgt gga      1824
Pro Trp Gln Val Ser Leu Arg Thr Arg Phe Gly Met His Phe Cys Gly
        595                 600                 605 ggc acc ttg ata tcc cca gag tgg gtg ttg act gct gcc cac tgc ttg      1872
Gly Thr Leu Ile Ser Pro Glu Trp Val Leu Thr Ala Ala His Cys Leu
    610                 615                 620 gag aag tcc cca agg cct tca tcc tac aag gtc atc ctg ggt gca cac      1920
Glu Lys Ser Pro Arg Pro Ser Ser Tyr Lys Val Ile Leu Gly Ala His
625                 630                 635                 640 caa gaa gtg aat ctc gaa ccg cat gtt cag gaa ata gaa gtg tct agg      1968
Gln Glu Val Asn Leu Glu Pro His Val Gln Glu Ile Glu Val Ser Arg
                645                 650                 655 ctg ttc ttg gag ccc aca cga aaa gat att gcc ttg cta aag cta agc      2016
Leu Phe Leu Glu Pro Thr Arg Lys Asp Ile Ala Leu Leu Lys Leu Ser
            660                 665                 670 agt cct gcc gtc atc act gac aaa gta atc cca gct tgt ctg cca tcc      2064
Ser Pro Ala Val Ile Thr Asp Lys Val Ile Pro Ala Cys Leu Pro Ser
        675                 680                 685
```

```
cca aat tat gtg gtc gct gac cgg acc gaa tgt ttc atc act ggc tgg    2112
Pro Asn Tyr Val Val Ala Asp Arg Thr Glu Cys Phe Ile Thr Gly Trp
    690             695                 700 gga gaa acc caa ggt act ttt gga gct ggc ctt ctc aag gaa gcc cag    2160
Gly Glu Thr Gln Gly Thr Phe Gly Ala Gly Leu Leu Lys Glu Ala Gln
705             710                 715                 720 ctc cct gtg att gag aat aaa gtg tgc aat cgc tat gag ttt ctg aat    2208
Leu Pro Val Ile Glu Asn Lys Val Cys Asn Arg Tyr Glu Phe Leu Asn
                725                 730                 735 gga aga gtc caa tcc acc gaa ctc tgt gct ggg cat ttg gcc gga ggc    2256
Gly Arg Val Gln Ser Thr Glu Leu Cys Ala Gly His Leu Ala Gly Gly
            740                 745                 750 act gac agt tgc cag ggt gac agt gga ggt cct ctg gtt tgc ttc gag    2304
Thr Asp Ser Cys Gln Gly Asp Ser Gly Gly Pro Leu Val Cys Phe Glu
        755                 760                 765 aag gac aaa tac att tta caa gga gtc act tct tgg ggt ctt ggc tgt    2352
Lys Asp Lys Tyr Ile Leu Gln Gly Val Thr Ser Trp Gly Leu Gly Cys
    770                 775                 780 gca cgc ccc aat aag cct ggt gtc tat gtt cgt gtt tca agg ttt gtt    2400
Ala Arg Pro Asn Lys Pro Gly Val Tyr Val Arg Val Ser Arg Phe Val
785             790                 795                 800 act tgg att gag gga gtg atg aga aat aat taa                        2433
Thr Trp Ile Glu Gly Val Met Arg Asn Asn
                805                 810

<210>  2
<211>  810
<212>  PRT
<213>  Homo sapiens
```

```
<400> 2

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Glu Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140
```

```
Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Arg Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300
```

```
His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
            325                 330                 335

Thr Thr Asn Ser Gln Val Arg Trp Glu Tyr Cys Lys Ile Pro Ser Cys
        340                 345                 350

Asp Ser Ser Pro Val Ser Thr Glu Gln Leu Ala Pro Thr Ala Pro Pro
    355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Gly Lys Lys Cys Gln Ser
385                 390                 395                 400

Trp Ser Ser Met Thr Pro His Arg His Gln Lys Thr Pro Glu Asn Tyr
            405                 410                 415

Pro Asn Ala Gly Leu Thr Met Asn Tyr Cys Arg Asn Pro Asp Ala Asp
        420                 425                 430

Lys Gly Pro Trp Cys Phe Thr Thr Asp Pro Ser Val Arg Trp Glu Tyr
    435                 440                 445

Cys Asn Leu Lys Lys Cys Ser Gly Thr Glu Ala Ser Val Val Ala Pro
450                 455                 460
```

```
Pro Pro Val Val Leu Leu Pro Asp Val Glu Thr Pro Ser Glu Glu Asp
465             470             475             480

Cys Met Phe Gly Asn Gly Lys Gly Tyr Arg Gly Lys Arg Ala Thr Thr
            485             490             495

Val Thr Gly Thr Pro Cys Gln Asp Trp Ala Ala Gln Glu Pro His Arg
            500             505             510

His Ser Ile Phe Thr Pro Glu Thr Asn Pro Arg Ala Gly Leu Glu Lys
            515             520             525

Asn Tyr Cys Arg Asn Pro Asp Gly Asp Val Gly Gly Pro Trp Cys Tyr
            530             535             540

Thr Thr Asn Pro Arg Lys Leu Tyr Asp Tyr Cys Asp Val Pro Gln Cys
545             550             555             560

Ala Ala Pro Ser Phe Asp Cys Gly Lys Pro Gln Val Glu Pro Lys Lys
            565             570             575

Cys Pro Gly Arg Val Val Gly Gly Cys Val Ala His Pro His Ser Trp
            580             585             590

Pro Trp Gln Val Ser Leu Arg Thr Arg Phe Gly Met His Phe Cys Gly
            595             600             605

Gly Thr Leu Ile Ser Pro Glu Trp Val Leu Thr Ala Ala His Cys Leu
            610             615             620
```

```
Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Lys Asp Ile Ala Leu Leu Lys Leu Ser
            660                 665                 670

Ser Pro Ala Val Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Gln Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780
```

```
        Ala Arg Pro Asn Lys Pro Gly Val Tyr Val Arg Val Ser Arg Phe Val
        785                 790                 795                 800

Thr Trp Ile Glu Gly Val Met Arg Asn Asn
                        805                 810

<210>  3
<211>  750
<212>  DNA
<213>  Homo sapiens

<220>
<221>  CDS
<222>  (1)..(750)

<400>  3
gcc cct tca ttt gat tgt ggg aag cct caa gtg gag ccg aag aaa tgt      48
Ala Pro Ser Phe Asp Cys Gly Lys Pro Gln Val Glu Pro Lys Lys Cys
1               5                   10                  15 cct gga agg gtt gtg ggg ggg tgt gtg gcc cac cca cat tcc tgg ccc      96
Pro Gly Arg Val Val Gly Gly Cys Val Ala His Pro His Ser Trp Pro
                20                  25                  30 tgg caa gtc agt ctt aga aca agg ttt gga atg cac ttc tgt gga ggc     144
Trp Gln Val Ser Leu Arg Thr Arg Phe Gly Met His Phe Cys Gly Gly
            35                  40                  45 acc ttg ata tcc cca gag tgg gtg ttg act gct gcc cac tgc ttg gag     192
Thr Leu Ile Ser Pro Glu Trp Val Leu Thr Ala Ala His Cys Leu Glu
        50                  55                  60 aag tcc cca agg cct tca tcc tac aag gtc atc ctg ggt gca cac caa     240
Lys Ser Pro Arg Pro Ser Ser Tyr Lys Val Ile Leu Gly Ala His Gln
65                  70                  75                  80
```

```
gaa gtg aat ctc gaa ccg cat gtt cag gaa ata gaa gtg tct agg ctg    288
Glu Val Asn Leu Glu Pro His Val Gln Glu Ile Glu Val Ser Arg Leu
                85                  90                  95 ttc ttg gag ccc aca cga aaa gat att gcc ttg cta aag cta agc agt    336
Phe Leu Glu Pro Thr Arg Lys Asp Ile Ala Leu Leu Lys Leu Ser Ser
               100                 105                 110 cct gcc gtc atc act gac aaa gta atc cca gct tgt ctg cca tcc cca    384
Pro Ala Val Ile Thr Asp Lys Val Ile Pro Ala Cys Leu Pro Ser Pro
               115                 120                 125 aat tat gtg gtc gct gac cgg acc gaa tgt ttc atc act ggc tgg gga    432
Asn Tyr Val Val Ala Asp Arg Thr Glu Cys Phe Ile Thr Gly Trp Gly
           130                 135                 140 gaa acc caa ggt act ttt gga gct ggc ctt ctc aag gaa gcc cag ctc    480
Glu Thr Gln Gly Thr Phe Gly Ala Gly Leu Leu Lys Glu Ala Gln Leu
145                 150                 155                 160 cct gtg att gag aat aaa gtg tgc aat cgc tat gag ttt ctg aat gga    528
Pro Val Ile Glu Asn Lys Val Cys Asn Arg Tyr Glu Phe Leu Asn Gly
                    165                 170                 175 aga gtc caa tcc acc gaa ctc tgt gct ggg cat ttg gcc gga ggc act    576
Arg Val Gln Ser Thr Glu Leu Cys Ala Gly His Leu Ala Gly Gly Thr
               180                 185                 190 gac agt tgc cag ggt gac agt gga ggt cct ctg gtt tgc ttc gag aag    624
Asp Ser Cys Gln Gly Asp Ser Gly Gly Pro Leu Val Cys Phe Glu Lys
           195                 200                 205 gac aaa tac att tta caa gga gtc act tct tgg ggt ctt ggc tgt gca    672
Asp Lys Tyr Ile Leu Gln Gly Val Thr Ser Trp Gly Leu Gly Cys Ala
210                 215                 220
```

```
cgc ccc aat aag cct ggt gtc tat gtt cgt gtt tca agg ttt gtt act    720
Arg Pro Asn Lys Pro Gly Val Tyr Val Arg Val Ser Arg Phe Val Thr
225                 230                 235                 240 tgg att gag gga gtg atg aga aat aat taa                            750
Trp Ile Glu Gly Val Met Arg Asn Asn
                245
```

<210> 4
<211> 249
<212> PRT
<213> Homo sapiens

<400> 4

```
Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
                20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95
```

```
Phe Leu Glu Pro Thr Arg Lys Asp Ile Ala Leu Leu Lys Leu Ser Ser
            100                 105             110

Pro Ala Val Ile Thr Asp Lys Val Ile Pro Ala Cys Leu Pro Ser Pro
        115                 120             125

Asn Tyr Val Val Ala Asp Arg Thr Glu Cys Phe Ile Thr Gly Trp Gly
    130                 135             140

Glu Thr Gln Gly Thr Phe Gly Ala Gly Leu Leu Lys Glu Ala Gln Leu
145                 150             155                 160

Pro Val Ile Glu Asn Lys Val Cys Asn Arg Tyr Glu Phe Leu Asn Gly
            165                 170             175

Arg Val Gln Ser Thr Glu Leu Cys Ala Gly His Leu Ala Gly Gly Thr
            180                 185             190

Asp Ser Cys Gln Gly Asp Ser Gly Gly Pro Leu Val Cys Phe Glu Lys
        195                 200             205

Asp Lys Tyr Ile Leu Gln Gly Val Thr Ser Trp Gly Leu Gly Cys Ala
        210                 215             220

Arg Pro Asn Lys Pro Gly Val Tyr Val Arg Val Ser Arg Phe Val Thr
225                 230             235                 240

Trp Ile Glu Gly Val Met Arg Asn Asn
                245
```

<210> 5
<211> 1047
<212> DNA
<213> Homo sapiens

<220>
<221> CDS
<222> (1)..(1047)

<400> 5

| | | | | | | | | | | | | | | | | |
|---|---|---|---|---|---|---|---|---|---|---|---|---|---|---|---|---|
| gca | cct | ccg | cct | gtt | gtc | ctg | ctt | cca | gat | gta | gag | act | cct | tcc | gaa | 48 |
| Ala | Pro | Pro | Pro | Val | Val | Leu | Leu | Pro | Asp | Val | Glu | Thr | Pro | Ser | Glu | |
| 1 | | | | 5 | | | | | 10 | | | | | 15 | | |

| gaa | gac | tgt | atg | ttt | ggg | aat | ggg | aaa | gga | tac | cga | ggc | aag | agg | gcg | 96 |
|---|---|---|---|---|---|---|---|---|---|---|---|---|---|---|---|---|
| Glu | Asp | Cys | Met | Phe | Gly | Asn | Gly | Lys | Gly | Tyr | Arg | Gly | Lys | Arg | Ala | |
| | | | 20 | | | | | 25 | | | | | 30 | | | |

| acc | act | gtt | act | ggg | acg | cca | tgc | cag | gac | tgg | gct | gcc | cag | gag | ccc | 144 |
|---|---|---|---|---|---|---|---|---|---|---|---|---|---|---|---|---|
| Thr | Thr | Val | Thr | Gly | Thr | Pro | Cys | Gln | Asp | Trp | Ala | Ala | Gln | Glu | Pro | |
| | | 35 | | | | | 40 | | | | | 45 | | | | |

| cat | aga | cac | agc | att | ttc | act | cca | gag | aca | aat | cca | cgg | gcg | ggt | ctg | 192 |
|---|---|---|---|---|---|---|---|---|---|---|---|---|---|---|---|---|
| His | Arg | His | Ser | Ile | Phe | Thr | Pro | Glu | Thr | Asn | Pro | Arg | Ala | Gly | Leu | |
| | 50 | | | | | 55 | | | | | 60 | | | | | |

| gaa | aaa | aat | tac | tgc | cgt | aac | cct | gat | ggt | gat | gta | ggt | ggt | ccc | tgg | 240 |
|---|---|---|---|---|---|---|---|---|---|---|---|---|---|---|---|---|
| Glu | Lys | Asn | Tyr | Cys | Arg | Asn | Pro | Asp | Gly | Asp | Val | Gly | Gly | Pro | Trp | |
| 65 | | | | 70 | | | | | 75 | | | | | 80 | | |

| tgc | tac | acg | aca | aat | cca | aga | aaa | ctt | tac | gac | tac | tgt | gat | gtc | cct | 288 |
|---|---|---|---|---|---|---|---|---|---|---|---|---|---|---|---|---|
| Cys | Tyr | Thr | Thr | Asn | Pro | Arg | Lys | Leu | Tyr | Asp | Tyr | Cys | Asp | Val | Pro | |
| | | | 85 | | | | | 90 | | | | | 95 | | | |

| cag | tgt | gcg | gcc | cct | tca | ttt | gat | tgt | ggg | aag | cct | caa | gtg | gag | ccg | 336 |
|---|---|---|---|---|---|---|---|---|---|---|---|---|---|---|---|---|
| Gln | Cys | Ala | Ala | Pro | Ser | Phe | Asp | Cys | Gly | Lys | Pro | Gln | Val | Glu | Pro | |
| | | | 100 | | | | | 105 | | | | | 110 | | | |

```
aag aaa tgt cct gga agg gtt gtg ggg ggg tgt gtg gcc cac cca cat      384
Lys Lys Cys Pro Gly Arg Val Val Gly Gly Cys Val Ala His Pro His
        115                 120                 125 tcc tgg ccc tgg caa gtc agt ctt aga aca agg ttt gga atg cac ttc      432
Ser Trp Pro Trp Gln Val Ser Leu Arg Thr Arg Phe Gly Met His Phe
        130                 135                 140 tgt gga ggc acc ttg ata tcc cca gag tgg gtg ttg act gct gcc cac      480
Cys Gly Gly Thr Leu Ile Ser Pro Glu Trp Val Leu Thr Ala Ala His
145                 150                 155                 160 tgc ttg gag aag tcc cca agg cct tca tcc tac aag gtc atc ctg ggt      528
Cys Leu Glu Lys Ser Pro Arg Pro Ser Ser Tyr Lys Val Ile Leu Gly
                165                 170                 175 gca cac caa gaa gtg aat ctc gaa ccg cat gtt cag gaa ata gaa gtg      576
Ala His Gln Glu Val Asn Leu Glu Pro His Val Gln Glu Ile Glu Val
            180                 185                 190 tct agg ctg ttc ttg gag ccc aca cga aaa gat att gcc ttg cta aag      624
Ser Arg Leu Phe Leu Glu Pro Thr Arg Lys Asp Ile Ala Leu Leu Lys
        195                 200                 205 cta agc agt cct gcc gtc atc act gac aaa gta atc cca gct tgt ctg      672
Leu Ser Ser Pro Ala Val Ile Thr Asp Lys Val Ile Pro Ala Cys Leu
210                 215                 220 cca tcc cca aat tat gtg gtc gct gac cgg acc gaa tgt ttc atc act      720
Pro Ser Pro Asn Tyr Val Val Ala Asp Arg Thr Glu Cys Phe Ile Thr
225                 230                 235                 240 ggc tgg gga gaa acc caa ggt act ttt gga gct ggc ctt ctc aag gaa      768
Gly Trp Gly Glu Thr Gln Gly Thr Phe Gly Ala Gly Leu Leu Lys Glu
                245                 250                 255
```

```
gcc cag ctc cct gtg att gag aat aaa gtg tgc aat cgc tat gag ttt      816
Ala Gln Leu Pro Val Ile Glu Asn Lys Val Cys Asn Arg Tyr Glu Phe
            260                 265                 270 ctg aat gga aga gtc caa tcc acc gaa ctc tgt gct ggg cat ttg gcc      864
Leu Asn Gly Arg Val Gln Ser Thr Glu Leu Cys Ala Gly His Leu Ala
        275                 280                 285 gga ggc act gac agt tgc cag ggt gac agt gga ggt cct ctg gtt tgc      912
Gly Gly Thr Asp Ser Cys Gln Gly Asp Ser Gly Gly Pro Leu Val Cys
    290                 295                 300 ttc gag aag gac aaa tac att tta caa gga gtc act tct tgg ggt ctt      960
Phe Glu Lys Asp Lys Tyr Ile Leu Gln Gly Val Thr Ser Trp Gly Leu
305                 310                 315                 320 ggc tgt gca cgc ccc aat aag cct ggt gtc tat gtt cgt gtt tca agg     1008
Gly Cys Ala Arg Pro Asn Lys Pro Gly Val Tyr Val Arg Val Ser Arg
                325                 330                 335 ttt gtt act tgg att gag gga gtg atg aga aat aat taa                 1047
Phe Val Thr Trp Ile Glu Gly Val Met Arg Asn Asn
                340                 345

<210>  6
<211>  348
<212>  PRT
<213>  Homo sapiens

<400>  6

Ala Pro Pro Val Val Leu Leu Pro Asp Val Glu Thr Pro Ser Glu
1               5                   10                  15
```

```
Glu Asp Cys Met Phe Gly Asn Gly Lys Gly Tyr Arg Gly Lys Arg Ala
             20                  25                  30

Thr Thr Val Thr Gly Thr Pro Cys Gln Asp Trp Ala Ala Gln Glu Pro
         35                  40                  45

His Arg His Ser Ile Phe Thr Pro Glu Thr Asn Pro Arg Ala Gly Leu
     50                  55                  60

Glu Lys Asn Tyr Cys Arg Asn Pro Asp Gly Asp Val Gly Gly Pro Trp
 65              70                  75                      80

Cys Tyr Thr Thr Asn Pro Arg Lys Leu Tyr Asp Tyr Cys Asp Val Pro
             85                  90                  95

Gln Cys Ala Ala Pro Ser Phe Asp Cys Gly Lys Pro Gln Val Glu Pro
             100                 105                 110

Lys Lys Cys Pro Gly Arg Val Val Gly Gly Cys Val Ala His Pro His
         115                 120                 125

Ser Trp Pro Trp Gln Val Ser Leu Arg Thr Arg Phe Gly Met His Phe
         130             135                 140

Cys Gly Gly Thr Leu Ile Ser Pro Glu Trp Val Leu Thr Ala Ala His
 145             150                 155                     160

Cys Leu Glu Lys Ser Pro Arg Pro Ser Ser Tyr Lys Val Ile Leu Gly
             165                 170                 175
```

```
Ala His Gln Glu Val Asn Leu Glu Pro His Val Gln Glu Ile Glu Val
        180                 185                 190

Ser Arg Leu Phe Leu Glu Pro Thr Arg Lys Asp Ile Ala Leu Leu Lys
        195                 200                 205

Leu Ser Ser Pro Ala Val Ile Thr Asp Lys Val Ile Pro Ala Cys Leu
        210                 215                 220

Pro Ser Pro Asn Tyr Val Ala Asp Arg Thr Glu Cys Phe Ile Thr
225                 230                 235                 240

Gly Trp Gly Glu Thr Gln Gly Thr Phe Gly Ala Gly Leu Leu Lys Glu
                245                 250                 255

Ala Gln Leu Pro Val Ile Glu Asn Lys Val Cys Asn Arg Tyr Glu Phe
                260                 265                 270

Leu Asn Gly Arg Val Gln Ser Thr Glu Leu Cys Ala Gly His Leu Ala
        275                 280                 285

Gly Gly Thr Asp Ser Cys Gln Gly Asp Ser Gly Gly Pro Leu Val Cys
    290                 295                 300

Phe Glu Lys Asp Lys Tyr Ile Leu Gln Gly Val Thr Ser Trp Gly Leu
305                 310                 315                 320

Gly Cys Ala Arg Pro Asn Lys Pro Gly Val Tyr Val Arg Val Ser Arg
                325                 330                 335
```

```
    Phe Val Thr Trp Ile Glu Gly Val Met Arg Asn Asn
                340                 345

<210> 7
<211> 38
<212> DNA
<213> Homo sapiens

<220>
<221> misc_feature
<222> (1)..(38)

<400> 7
ggggtatctc tcgagaaaag agccccttca tttgattg                              38

<210> 8
<211> 38
<212> DNA
<213> Homo sapiens

<220>
<221> misc_feature
<222> (1)..(38)
<223> reverse primer human microplasminogen <400> 8
gtttttgttc tagattaatt atttctcatc actccctc                              38

<210> 9
<211> 47
<212> DNA
<213> Homo sapiens
```

```
<220>
<221> misc_feature
<222> (1)..(47)
<223> forward primer human miniplasminogen <400> 9
ggggtatctc tcgagaaaag agcacctccg cctgttgtcc tgcttcc        47

<210> 10
<211> 27
<212> DNA
<213> Homo sapiens

<220>
<221> misc_feature
<222> (1)..(27)
<223> reverse primer human miniplasminogen <400> 10
gcagtgggct gcagtcaaca cccactc                              27

<210> 11
<211> 7
<212> PRT
<213> Artificial Sequence

<220>
<223> synthetic

<400> 11

Glu Lys Arg Glu Ala Glu Ala
1               5
```

```
<210>  12
<211>  6
<212>  PRT
<213>  Artificial Sequence

<220>
<223>  synthetic

<400>  12

Ala Pro Ser Phe Asp Cys
1               5

<210>  13
<211>  4
<212>  PRT
<213>  Artificial Sequence

<220>
<223>  synthetic

<400>  13

Leu Glu Lys Arg
1

<210>  14
<211>  9
<212>  PRT
<213>  Artificial Sequence

<220>
<223>  synthetic

<400>  14
```

```
Ala Pro Pro Pro Val Val Leu Leu Pro
1               5

<210> 15
<211> 9
<212> PRT
<213> Artificial Sequence

<220>
<223> synthetic

<400> 15

Glu Trp Val Leu Thr Ala Ala His Cys
1               5
```

Column 37, in Claim 6, replace "claim 4, belonging" with --claim 4, said yeast cell belonging--.

Column 38,
    in Claim 9, replace "claim 1, expressing" with --claim 1, said yeast cell expressing--.
    in Claim 9, replace "100 mg/litre" with --100 mg/liter--.
    in Claim 10, replace "secretion signal." with --secretion signal sequence--.

Column 39, in Claim 19, replace "mammalian protein obtained" with --mammalian microplasmin obtained--.

Column 40,
    in Claim 23, replace "100 mg/litre." with --100 mg/liter.--.
    in Claim 26, replace "isolated cell" with --isolated host cell--.
    in Claim 28, replace "isolated cell" with --isolated host cell--.
    in Claim 30, replace ""isolated cell" with --isolated host cell--.